(12) United States Patent
Kale et al.

(10) Patent No.: US 8,840,677 B2
(45) Date of Patent: Sep. 23, 2014

(54) ALLOGRAFT BONE PLUGS, SYSTEMS AND TECHNIQUES

(75) Inventors: Shreedhar Kale, West Chester, PA (US);
Dennis Chien, West Chester, PA (US);
Robert Delurio, West Chester, PA (US);
Curtis Compton, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 200 days.

(21) Appl. No.: 12/945,156

(22) Filed: Nov. 12, 2010

(65) Prior Publication Data

US 2011/0144766 A1 Jun. 16, 2011

Related U.S. Application Data

(63) Continuation-in-part of application No. PCT/US2009/048055, filed on Jun. 19, 2009.

(60) Provisional application No. 61/073,998, filed on Jun. 19, 2008, provisional application No. 61/106,862, filed on Oct. 20, 2008.

(51) Int. Cl.
*A61F 2/28* (2006.01)
*A61B 17/04* (2006.01)
*A61B 17/68* (2006.01)
*F16B 13/00* (2006.01)

(52) U.S. Cl.
CPC ......... *A61B 17/686* (2013.01); *F16B 2013/009* (2013.01)
USPC ...................................... 623/23.63; 606/313

(58) Field of Classification Search
USPC .......... 623/16.11, 17.11–17.16, 18.11, 14.12, 623/23.72–23.76, 23.63, 23.48; 606/302, 606/301, 314, 290, 291, 326–327, 323, 313, 606/300; 411/37
See application file for complete search history.

(56) References Cited

U.S. PATENT DOCUMENTS

| | | | | | |
|---|---|---|---|---|---|
| 1,752,752 | A | * | 4/1930 | Ogden | 411/68 |
| 2,381,050 | A | * | 8/1945 | Hardinge | 606/65 |
| 2,699,774 | A | * | 1/1955 | Livingston | 606/65 |
| 3,174,387 | A | * | 3/1965 | Fischer | 411/37 |
| 3,199,398 | A | * | 8/1965 | Weisz | 411/80.1 |
| 3,232,163 | A | * | 2/1966 | Croessant | 411/80.1 |
| 3,516,324 | A | * | 6/1970 | Berner | 411/72 |
| 3,601,869 | A | * | 8/1971 | Flora et al. | 411/548 |
| 3,765,295 | A | * | 10/1973 | Ptak | 411/41 |
| 3,789,728 | A | * | 2/1974 | Shackelford | 411/34 |

(Continued)

FOREIGN PATENT DOCUMENTS

| | | |
|---|---|---|
| DE | 29501042 U1 | 3/1995 |
| DE | 19605735 A1 | 6/1997 |

(Continued)

*Primary Examiner* — Alvin Stewart
(74) *Attorney, Agent, or Firm* — Baker & Hostetler LLP

(57) ABSTRACT

The present invention provides a system, device, instruments and methods for inserting and/or improving the holding strength and purchase of a bone screw, bone pin, or bone dowel in bone. Embodiments include monolithic allograft tissue forms, multi-piece allograft tissue forms, distally expandable portions, partially and fully demineralized portions, and flexible connecting portions. Advantages of the allograft tissue forms of the present invention include improved pedicle screw blackout strength and improved filling of bone voids. Methods for making and instruments and techniques for inserting the augmentation device, system and screws or pins are also disclosed.

53 Claims, 20 Drawing Sheets

(56) References Cited

U.S. PATENT DOCUMENTS

| | | | | |
|---|---|---|---|---|
| 3,797,358 | A * | 3/1974 | Allender | 411/38 |
| 3,832,931 | A * | 9/1974 | Talan | 411/80.2 |
| 3,896,504 | A * | 7/1975 | Fischer | 623/22.36 |
| 4,011,602 | A * | 3/1977 | Rybicki et al. | 623/23.76 |
| 4,276,806 | A * | 7/1981 | Morel | 411/41 |
| 4,312,612 | A * | 1/1982 | Thompson | 411/15 |
| 4,611,581 | A * | 9/1986 | Steffee | 606/292 |
| 4,716,893 | A * | 1/1988 | Fischer et al. | 606/66 |
| 4,760,843 | A * | 8/1988 | Fischer et al. | 606/304 |
| 4,789,285 | A * | 12/1988 | Fischer | 411/32 |
| 4,790,304 | A * | 12/1988 | Rosenberg | 606/916 |
| 4,932,973 | A * | 6/1990 | Gendler | 623/23.63 |
| 5,018,919 | A * | 5/1991 | Stephan | 411/33 |
| 5,041,116 | A * | 8/1991 | Wilson | 606/65 |
| 5,059,193 | A * | 10/1991 | Kuslich | 606/247 |
| 5,074,871 | A * | 12/1991 | Groshong | 606/170 |
| 5,084,050 | A * | 1/1992 | Draenert | 606/77 |
| 5,163,961 | A * | 11/1992 | Harwin | 623/22.46 |
| 5,209,753 | A | 5/1993 | Biedermann | |
| 5,211,647 | A | 5/1993 | Schmieding | |
| 5,224,805 | A * | 7/1993 | Moretti et al. | 411/30 |
| 5,268,001 | A | 12/1993 | Nicholson | |
| 5,298,254 | A * | 3/1994 | Prewett et al. | 424/422 |
| 5,312,215 | A * | 5/1994 | Anquetin | 411/38 |
| 5,314,476 | A * | 5/1994 | Prewett et al. | 623/23.63 |
| 5,324,292 | A * | 6/1994 | Meyers | 606/916 |
| 5,326,205 | A * | 7/1994 | Anspach et al. | 411/43 |
| 5,360,450 | A * | 11/1994 | Giannini | 623/21.19 |
| 5,375,954 | A * | 12/1994 | Eguchi | 411/48 |
| 5,397,328 | A * | 3/1995 | Behrens et al. | 606/63 |
| 5,439,684 | A * | 8/1995 | Prewett et al. | 424/422 |
| 5,454,365 | A * | 10/1995 | Bonutti | 600/204 |
| 5,454,811 | A * | 10/1995 | Huebner | 606/60 |
| 5,464,427 | A * | 11/1995 | Curtis et al. | 606/232 |
| 5,489,210 | A * | 2/1996 | Hanosh | 433/173 |
| 5,578,035 | A * | 11/1996 | Lin | 606/68 |
| 5,601,558 | A * | 2/1997 | Torrie et al. | 606/326 |
| 5,632,748 | A * | 5/1997 | Beck et al. | 606/89 |
| 5,645,589 | A * | 7/1997 | Li | 606/60 |
| 5,702,397 | A * | 12/1997 | Goble et al. | 606/232 |
| 5,707,395 | A * | 1/1998 | Li | 606/232 |
| 5,713,904 | A * | 2/1998 | Errico et al. | 606/327 |
| 5,720,753 | A * | 2/1998 | Sander et al. | 606/104 |
| 5,725,529 | A * | 3/1998 | Nicholson et al. | 606/232 |
| 5,755,720 | A | 5/1998 | Mikhail | |
| 5,759,184 | A * | 6/1998 | Santangelo | 606/68 |
| 5,782,865 | A | 7/1998 | Grotz | |
| 5,797,963 | A * | 8/1998 | McDevitt | 606/232 |
| 5,910,315 | A * | 6/1999 | Stevenson et al. | 424/422 |
| 5,919,194 | A * | 7/1999 | Anderson | 606/313 |
| 5,935,129 | A * | 8/1999 | McDevitt et al. | 606/232 |
| 5,957,953 | A * | 9/1999 | DiPoto et al. | 606/232 |
| 5,961,520 | A * | 10/1999 | Beck et al. | 606/232 |
| 5,968,047 | A * | 10/1999 | Reed | 606/76 |
| 6,001,102 | A | 12/1999 | Alacreu | |
| 6,039,740 | A * | 3/2000 | Olerud | 606/309 |
| 6,049,026 | A * | 4/2000 | Muschler | 424/93.7 |
| 6,056,750 | A * | 5/2000 | Lob | 606/326 |
| 6,090,998 | A * | 7/2000 | Grooms et al. | 128/898 |
| 6,123,731 | A * | 9/2000 | Boyce et al. | 623/23.63 |
| 6,200,323 | B1 | 3/2001 | Pierson, III | |
| 6,206,923 | B1 * | 3/2001 | Boyd et al. | 623/17.11 |
| 6,231,606 | B1 | 5/2001 | Graf | |
| 6,235,031 | B1 * | 5/2001 | Hodgeman et al. | 606/64 |
| 6,241,732 | B1 * | 6/2001 | Overaker et al. | 606/327 |
| 6,290,701 | B1 * | 9/2001 | Enayati | 606/327 |
| 6,294,041 | B1 * | 9/2001 | Boyce et al. | 156/275.5 |
| 6,299,642 | B1 * | 10/2001 | Chan | 623/16.11 |
| 6,336,940 | B1 * | 1/2002 | Graf et al. | 623/13.14 |
| 6,355,044 | B1 * | 3/2002 | Hair | 606/326 |
| 6,398,811 | B1 * | 6/2002 | McKay | 623/17.16 |
| 6,443,954 | B1 * | 9/2002 | Bramlet et al. | 606/62 |
| 6,517,579 | B1 * | 2/2003 | Paulos et al. | 623/13.14 |
| 6,533,816 | B2 * | 3/2003 | Sklar | 623/13.14 |
| 6,554,830 | B1 * | 4/2003 | Chappius | 606/246 |
| 6,558,094 | B2 * | 5/2003 | Nehl | 411/36 |
| 6,575,976 | B2 * | 6/2003 | Grafton | 606/916 |
| 6,582,453 | B1 * | 6/2003 | Tran et al. | 606/232 |
| 6,602,034 | B2 * | 8/2003 | Wakai et al. | 411/37 |
| 6,623,492 | B1 * | 9/2003 | Berube et al. | 606/151 |
| 6,632,245 | B2 * | 10/2003 | Kim | 623/13.14 |
| 6,632,247 | B2 * | 10/2003 | Boyer et al. | 623/23.6 |
| 6,638,310 | B2 * | 10/2003 | Lin et al. | 623/17.11 |
| 6,641,596 | B1 * | 11/2003 | Lizardi | 606/232 |
| 6,648,893 | B2 | 11/2003 | Dudasik | |
| 6,652,593 | B2 * | 11/2003 | Boyer et al. | 623/23.63 |
| 6,660,008 | B1 * | 12/2003 | Foerster et al. | 606/327 |
| 6,660,038 | B2 * | 12/2003 | Boyer et al. | 623/17.15 |
| 6,676,665 | B2 * | 1/2004 | Foley et al. | 606/105 |
| 6,695,851 | B2 * | 2/2004 | Zdeblick et al. | 606/96 |
| 6,696,073 | B2 * | 2/2004 | Boyce et al. | 424/422 |
| 6,767,369 | B2 * | 7/2004 | Boyer, II et al. | 623/23.63 |
| 6,770,073 | B2 * | 8/2004 | McDevitt et al. | 606/60 |
| 6,840,770 | B2 * | 1/2005 | McDevitt | 433/173 |
| 6,855,167 | B2 * | 2/2005 | Shimp et al. | 623/17.11 |
| 6,893,462 | B2 * | 5/2005 | Buskirk et al. | 623/13.17 |
| 6,913,621 | B2 * | 7/2005 | Boyd et al. | 623/17.11 |
| 6,939,379 | B2 * | 9/2005 | Sklar | 623/13.14 |
| 7,074,203 | B1 * | 7/2006 | Johanson et al. | 602/72 |
| 7,083,647 | B1 * | 8/2006 | Sklar et al. | 623/13.14 |
| 7,087,056 | B2 * | 8/2006 | Vaughan | 606/86 A |
| 7,087,082 | B2 * | 8/2006 | Paul et al. | 623/17.11 |
| 7,094,239 | B1 * | 8/2006 | Michelson | 606/70 |
| 7,115,146 | B2 * | 10/2006 | Boyer et al. | 623/23.63 |
| 7,141,066 | B2 * | 11/2006 | Steiner et al. | 623/13.12 |
| 7,144,415 | B2 * | 12/2006 | Del Rio et al. | 606/232 |
| 7,156,880 | B2 * | 1/2007 | Evans et al. | 623/23.51 |
| 7,166,107 | B2 | 1/2007 | Anderson | |
| 7,201,754 | B2 | 4/2007 | Stewart | |
| 7,201,773 | B2 * | 4/2007 | Steiner et al. | 623/13.14 |
| 7,235,100 | B2 | 6/2007 | Martinek | |
| 7,300,465 | B2 * | 11/2007 | Paul et al. | 623/17.11 |
| 7,309,356 | B2 * | 12/2007 | Steiner | 623/13.14 |
| 7,331,962 | B2 | 2/2008 | Branemark | |
| 7,608,113 | B2 * | 10/2009 | Boyer et al. | 623/23.63 |
| 7,648,524 | B2 * | 1/2010 | Zhang et al. | 606/323 |
| 7,651,528 | B2 * | 1/2010 | Montgomery et al. | 623/13.14 |
| 7,662,185 | B2 * | 2/2010 | Alfaro et al. | 623/17.16 |
| 7,758,642 | B2 * | 7/2010 | Bojarski et al. | 623/13.14 |
| 7,828,848 | B2 * | 11/2010 | Chauvin et al. | 623/17.16 |
| 7,837,740 | B2 * | 11/2010 | Semler et al. | 623/23.63 |
| 7,850,717 | B2 * | 12/2010 | Dewey et al. | 606/246 |
| 7,857,840 | B2 * | 12/2010 | Krebs et al. | 606/327 |
| 7,879,103 | B2 * | 2/2011 | Gertzman et al. | 623/17.16 |
| 7,892,265 | B2 * | 2/2011 | Perez-Cruet et al. | 606/300 |
| 7,931,840 | B2 * | 4/2011 | Michelson | 264/162 |
| 7,955,388 | B2 * | 6/2011 | Jensen et al. | 623/13.14 |
| 7,967,851 | B2 * | 6/2011 | Bickley et al. | 606/313 |
| 7,976,861 | B2 * | 7/2011 | Reddi | 424/423 |
| 7,981,156 | B2 * | 7/2011 | Pafford et al. | 623/17.11 |
| 7,985,258 | B2 * | 7/2011 | Zdeblick et al. | 623/17.16 |
| 8,007,533 | B2 * | 8/2011 | Zhukauskas et al. | 623/13.14 |
| 8,034,090 | B2 * | 10/2011 | Stone et al. | 606/321 |
| 8,057,524 | B2 * | 11/2011 | Meridew | 606/321 |
| 8,062,295 | B2 * | 11/2011 | McDevitt et al. | 606/60 |
| 8,080,044 | B2 * | 12/2011 | Biedermann et al. | 606/313 |
| 8,105,379 | B2 * | 1/2012 | Carter et al. | 623/13.17 |
| 8,128,658 | B2 * | 3/2012 | Kaiser et al. | 606/232 |
| 8,128,670 | B2 * | 3/2012 | Ralph et al. | 606/313 |
| 8,133,421 | B2 * | 3/2012 | Boyce et al. | 264/109 |
| 8,163,032 | B2 * | 4/2012 | Evans et al. | 623/23.51 |
| 8,167,943 | B2 * | 5/2012 | Carter et al. | 623/13.17 |
| 8,177,848 | B2 * | 5/2012 | McKay | 623/17.16 |
| 8,221,479 | B2 * | 7/2012 | Glazer et al. | 606/326 |
| 8,226,714 | B2 * | 7/2012 | Beck et al. | 623/13.12 |
| 8,292,932 | B2 * | 10/2012 | Matthis et al. | 606/300 |
| 8,292,968 | B2 * | 10/2012 | Truncale et al. | 623/23.51 |
| 8,298,262 | B2 * | 10/2012 | Stone et al. | 606/232 |
| 8,317,825 | B2 * | 11/2012 | Stone | 606/213 |
| 8,323,543 | B2 * | 12/2012 | Michelson | 264/162 |
| 8,337,531 | B2 * | 12/2012 | Johnson et al. | 606/279 |
| 8,414,647 | B2 * | 4/2013 | Baird et al. | 623/13.14 |
| 8,419,780 | B2 * | 4/2013 | Bickley et al. | 606/326 |
| 8,435,294 | B2 * | 5/2013 | Montgomery et al. | 623/13.14 |

(56) References Cited

U.S. PATENT DOCUMENTS

| | | | |
|---|---|---|---|
| 2001/0051807 A1* | 12/2001 | Grafton | 606/72 |
| 2001/0053913 A1 | 12/2001 | Freedland | |
| 2002/0029084 A1* | 3/2002 | Paul et al. | 623/23.63 |
| 2002/0032445 A1* | 3/2002 | Fujiwara | 606/67 |
| 2002/0038123 A1* | 3/2002 | Visotsky et al. | 606/73 |
| 2002/0161449 A1* | 10/2002 | Muschler | 623/23.51 |
| 2003/0009235 A1* | 1/2003 | Manrique et al. | 623/23.63 |
| 2003/0023304 A1* | 1/2003 | Carter et al. | 623/13.14 |
| 2003/0045936 A1* | 3/2003 | Angelucci et al. | 623/17.11 |
| 2003/0187444 A1* | 10/2003 | Overaker et al. | 606/72 |
| 2003/0199877 A1* | 10/2003 | Steiger et al. | 606/72 |
| 2004/0034434 A1* | 2/2004 | Evans et al. | 623/23.51 |
| 2004/0167625 A1* | 8/2004 | Beyar et al. | 623/11.11 |
| 2004/0176767 A1* | 9/2004 | Bickley | 606/72 |
| 2004/0193162 A1* | 9/2004 | Bramlet et al. | 606/66 |
| 2004/0230193 A1* | 11/2004 | Cheung et al. | 606/63 |
| 2004/0254581 A1* | 12/2004 | Leclair | 606/73 |
| 2004/0267265 A1* | 12/2004 | Kyle | 606/73 |
| 2005/0177237 A1* | 8/2005 | Shappley et al. | 623/17.11 |
| 2005/0203622 A1* | 9/2005 | Steiner et al. | 623/13.14 |
| 2005/0216012 A1* | 9/2005 | Willmen | 606/72 |
| 2005/0240267 A1* | 10/2005 | Randall et al. | 623/17.11 |
| 2005/0283255 A1* | 12/2005 | Geremakis et al. | 623/23.51 |
| 2006/0004455 A1* | 1/2006 | Leonard et al. | 623/17.15 |
| 2006/0030948 A1* | 2/2006 | Manrique et al. | 623/23.13 |
| 2006/0074421 A1* | 4/2006 | Bickley et al. | 606/72 |
| 2006/0116685 A1 | 6/2006 | Urbanski | |
| 2006/0149258 A1* | 7/2006 | Sousa | 606/72 |
| 2006/0178752 A1* | 8/2006 | Yaccarino et al. | 623/23.63 |
| 2006/0195103 A1* | 8/2006 | Padget et al. | 606/72 |
| 2006/0200235 A1* | 9/2006 | Bianchi et al. | 623/13.14 |
| 2006/0204544 A1 | 9/2006 | Sunwoo | |
| 2006/0235410 A1* | 10/2006 | Ralph et al. | 606/72 |
| 2006/0235534 A1* | 10/2006 | Gertzman et al. | 623/17.16 |
| 2006/0247642 A1* | 11/2006 | Stone et al. | 606/73 |
| 2006/0276907 A1* | 12/2006 | Boyer et al. | 623/23.51 |
| 2007/0005072 A1* | 1/2007 | Castillo et al. | 606/79 |
| 2007/0038219 A1* | 2/2007 | Matthis et al. | 606/72 |
| 2007/0038221 A1* | 2/2007 | Fine et al. | 606/73 |
| 2007/0067034 A1* | 3/2007 | Chirico et al. | 623/17.11 |
| 2007/0118131 A1* | 5/2007 | Gooch | 606/72 |
| 2007/0162022 A1* | 7/2007 | Zhang et al. | 606/72 |
| 2007/0162132 A1 | 7/2007 | Messerli | |
| 2007/0173939 A1* | 7/2007 | Kim et al. | 623/17.11 |
| 2007/0191951 A1* | 8/2007 | Branch | 623/17.11 |
| 2008/0051887 A1* | 2/2008 | Carter et al. | 623/13.11 |
| 2008/0119859 A1* | 5/2008 | Lally | 606/76 |
| 2008/0133007 A1* | 6/2008 | Donnelly et al. | 623/13.14 |
| 2008/0133008 A1* | 6/2008 | Truncale et al. | 623/14.12 |
| 2008/0161806 A1* | 7/2008 | Donnelly et al. | 606/60 |
| 2008/0161864 A1* | 7/2008 | Beck et al. | 606/326 |
| 2008/0195204 A1* | 8/2008 | Zhukauskas et al. | 623/13.14 |
| 2008/0221623 A1* | 9/2008 | Gooch | 606/302 |
| 2008/0221624 A1* | 9/2008 | Gooch | 606/302 |
| 2008/0255621 A1* | 10/2008 | Fricker et al. | 606/302 |
| 2008/0255676 A1* | 10/2008 | Semler et al. | 623/23.51 |
| 2008/0262616 A1* | 10/2008 | McKay | 623/14.12 |
| 2008/0288003 A1* | 11/2008 | McKinley | 606/313 |
| 2008/0305145 A1* | 12/2008 | Shelby et al. | 424/423 |
| 2009/0005821 A1* | 1/2009 | Chirico et al. | 606/319 |
| 2009/0024223 A1* | 1/2009 | Chen et al. | 623/23.63 |
| 2009/0036896 A1* | 2/2009 | Krenkel et al. | 606/90 |
| 2009/0043342 A1* | 2/2009 | Freedland | 606/313 |
| 2009/0131992 A1* | 5/2009 | Greenhalgh et al. | 606/313 |
| 2009/0157124 A1* | 6/2009 | Ferragamo et al. | 606/301 |
| 2009/0312842 A1* | 12/2009 | Bursac et al. | 623/23.72 |
| 2010/0016905 A1* | 1/2010 | Greenhalgh et al. | 606/313 |
| 2010/0057208 A1* | 3/2010 | Dryer et al. | 623/17.16 |
| 2010/0069975 A1* | 3/2010 | Auge, II | 606/86 R |
| 2010/0082104 A1* | 4/2010 | Carter et al. | 623/13.14 |
| 2010/0145396 A1* | 6/2010 | Thornes | 606/313 |
| 2010/0203155 A1* | 8/2010 | Wei et al. | 424/549 |
| 2010/0215617 A1* | 8/2010 | Wasielewski | 424/85.2 |
| 2010/0226959 A1* | 9/2010 | Mckay | 424/425 |
| 2010/0228301 A1* | 9/2010 | Greenhalgh et al. | 606/313 |
| 2010/0241176 A1* | 9/2010 | Lob | 606/313 |
| 2010/0286780 A1* | 11/2010 | Dryer et al. | 623/17.11 |
| 2010/0286795 A1* | 11/2010 | Stone et al. | 623/23.72 |
| 2010/0324607 A1* | 12/2010 | Davis | 606/313 |
| 2011/0028945 A1* | 2/2011 | Amodei et al. | 604/890.1 |
| 2011/0040334 A1* | 2/2011 | Kaes et al. | 606/279 |
| 2011/0054408 A1* | 3/2011 | Wei et al. | 604/175 |
| 2011/0060373 A1* | 3/2011 | Russell et al. | 606/304 |
| 2011/0071579 A1* | 3/2011 | Reach, Jr. | 606/327 |
| 2011/0137418 A1* | 6/2011 | O'Neil et al. | 623/16.11 |
| 2011/0144766 A1* | 6/2011 | Kale et al. | 623/23.63 |
| 2011/0224797 A1* | 9/2011 | Semler et al. | 623/18.11 |
| 2011/0238124 A1* | 9/2011 | Richelsoph | 606/313 |
| 2012/0010668 A1* | 1/2012 | Shimko | 606/305 |
| 2012/0041395 A1* | 2/2012 | Sweeney | 604/272 |
| 2012/0046758 A1* | 2/2012 | Evans et al. | 623/23.61 |
| 2012/0059428 A1* | 3/2012 | Epperly | 606/310 |
| 2012/0071983 A1* | 3/2012 | Ray et al. | 623/17.16 |
| 2012/0207808 A1* | 8/2012 | Evans et al. | 424/426 |
| 2012/0259312 A1* | 10/2012 | Iannotti et al. | 604/506 |
| 2012/0259365 A1* | 10/2012 | Richelsoph | 623/13.14 |
| 2012/0283833 A1* | 11/2012 | Brannon | 623/16.11 |
| 2012/0310348 A1* | 12/2012 | Pafford et al. | 623/17.16 |
| 2012/0323324 A1* | 12/2012 | Buskirk et al. | 623/13.14 |

FOREIGN PATENT DOCUMENTS

| | | |
|---|---|---|
| EP | 0340159 B1 | 11/1989 |
| EP | 0409364 B1 | 1/1991 |
| EP | 1127581 A1 | 8/2001 |
| JP | 2003159258 A | 6/2003 |
| WO | WO 2004-105632 A1 | 12/2004 |
| WO | WO 2006099751 A1 | 9/2006 |
| WO | WO 2008004057 A2 | 1/2008 |

* cited by examiner

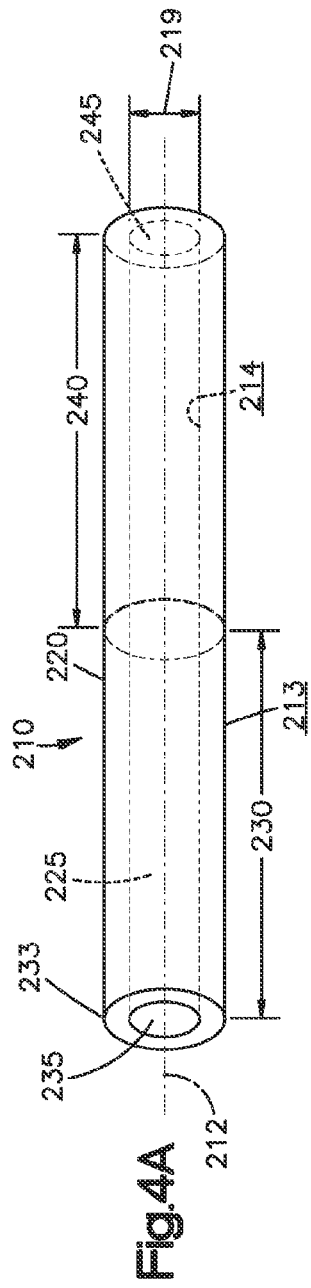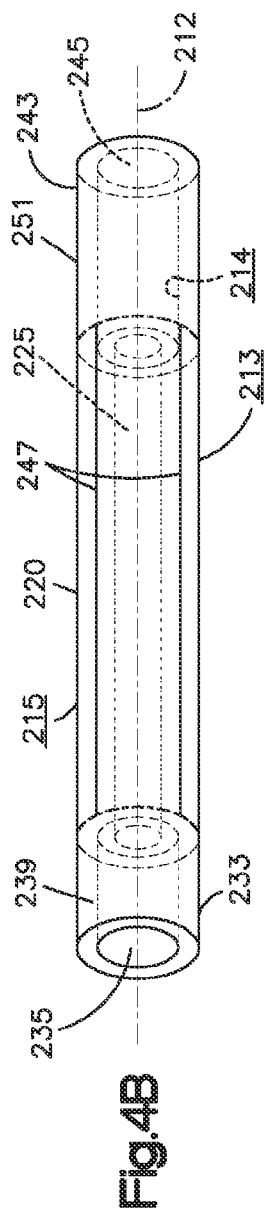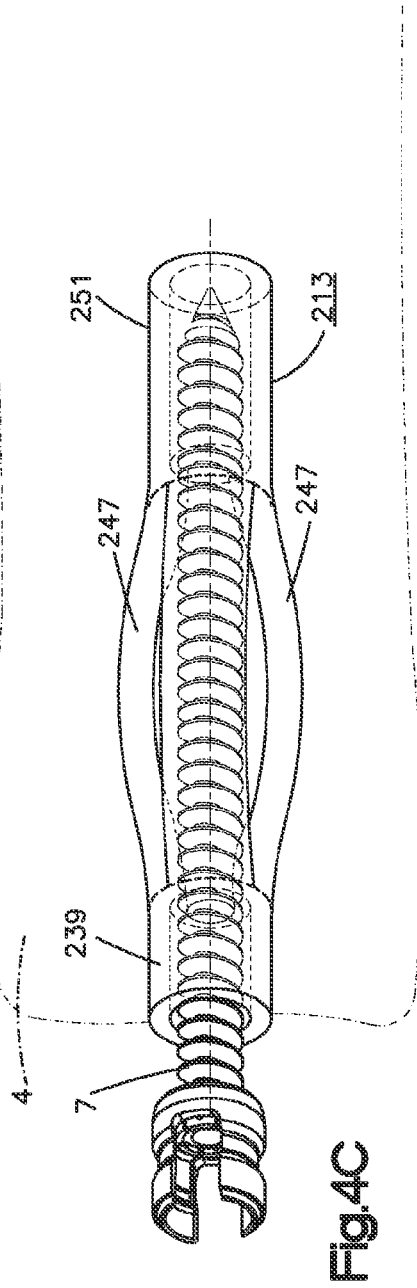

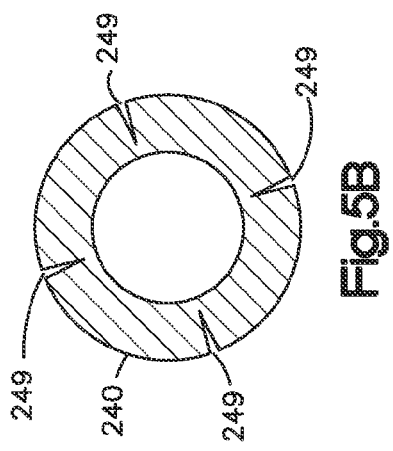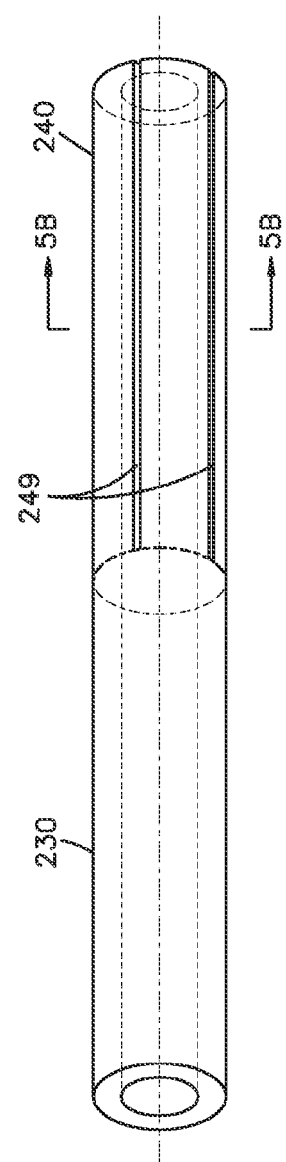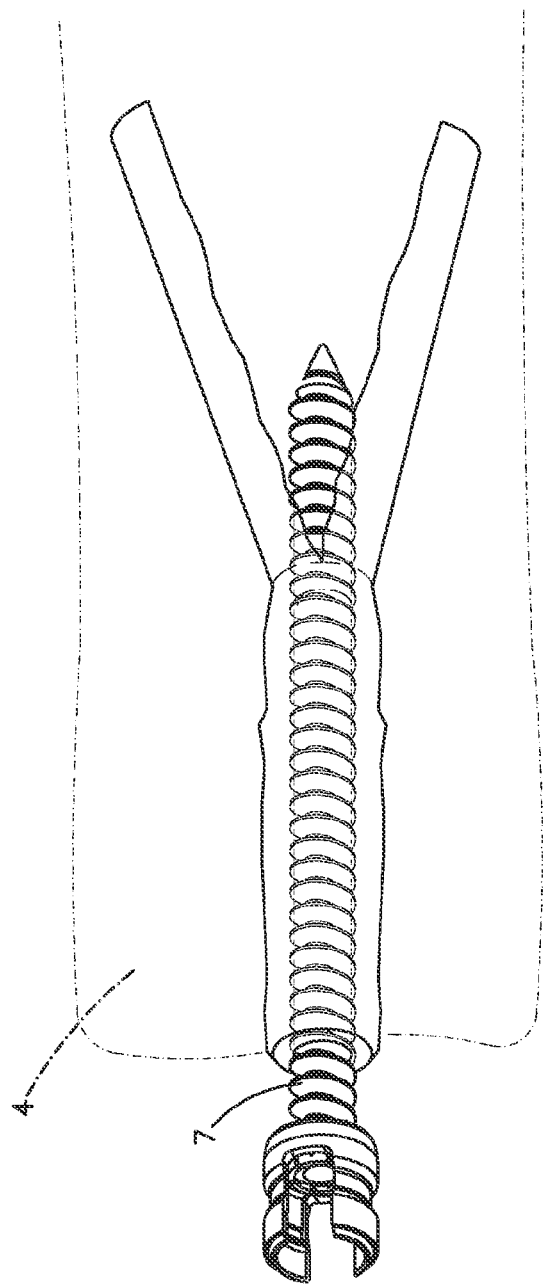

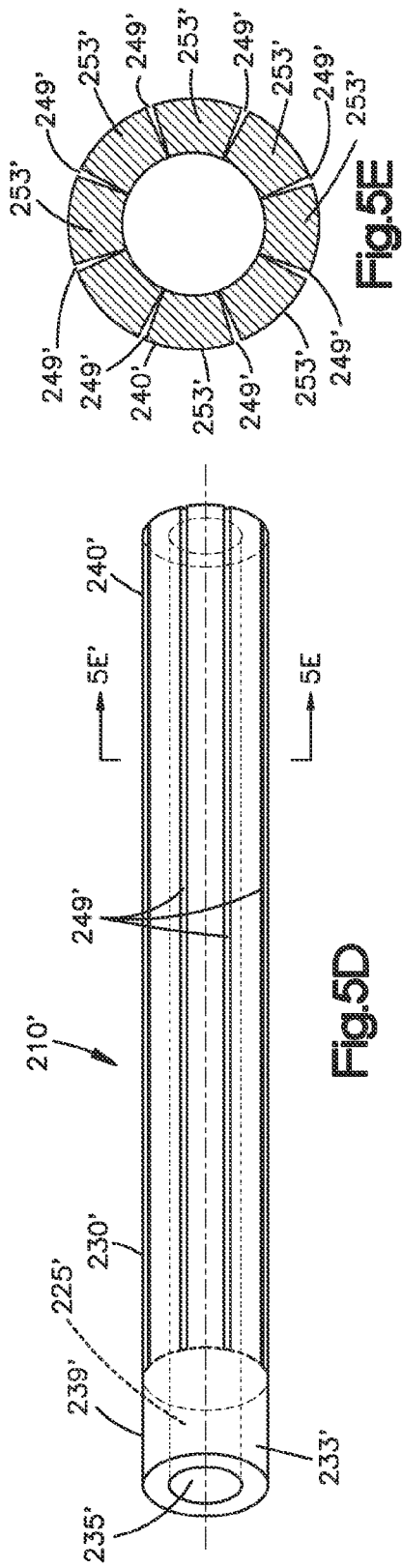
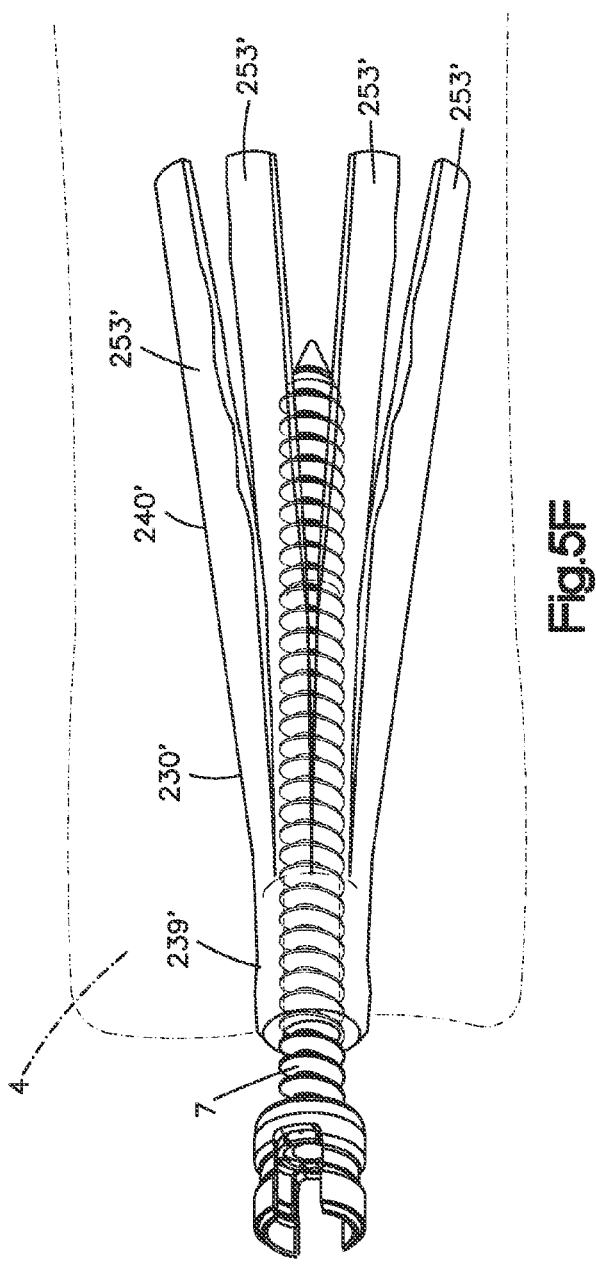

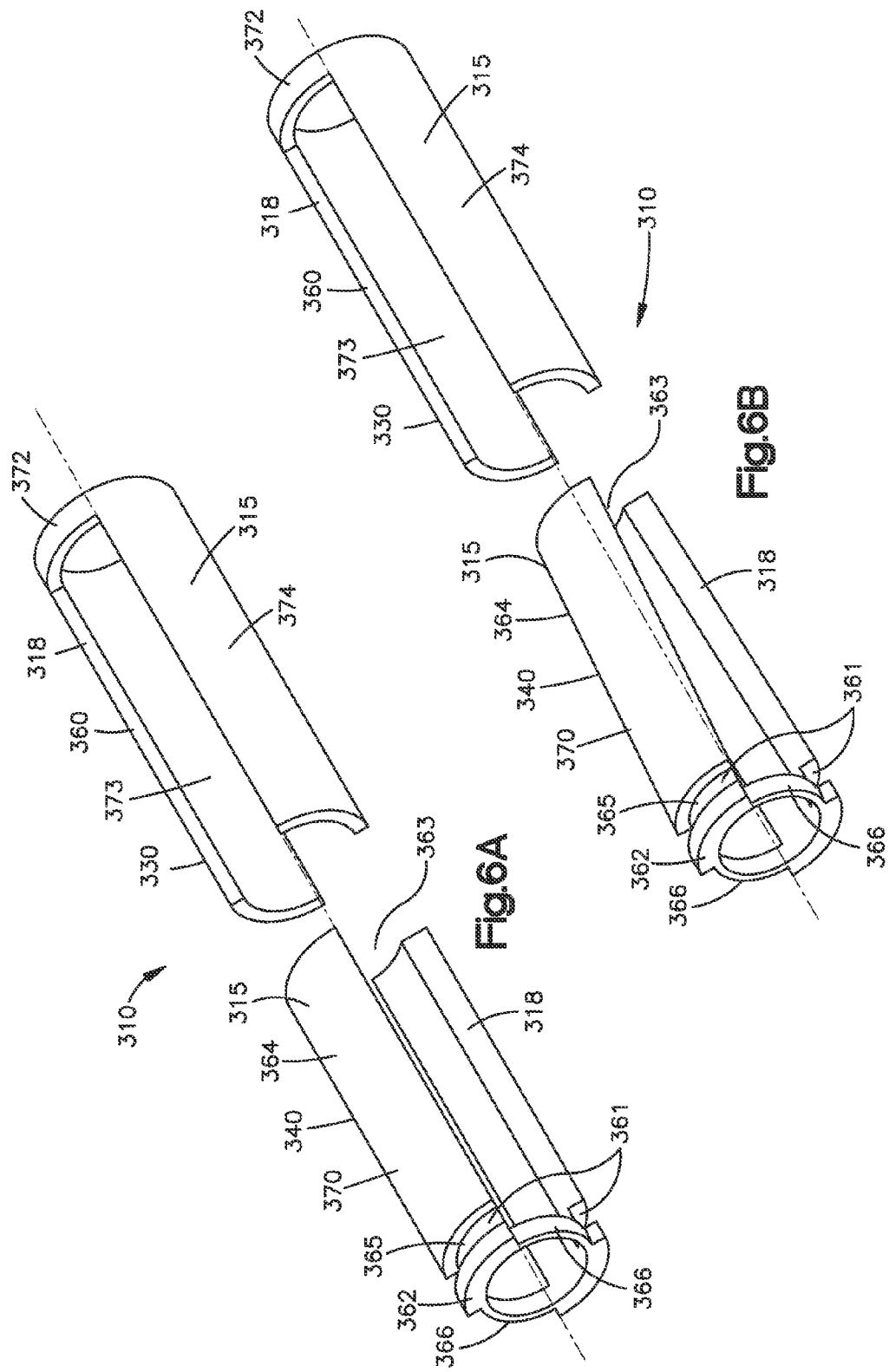

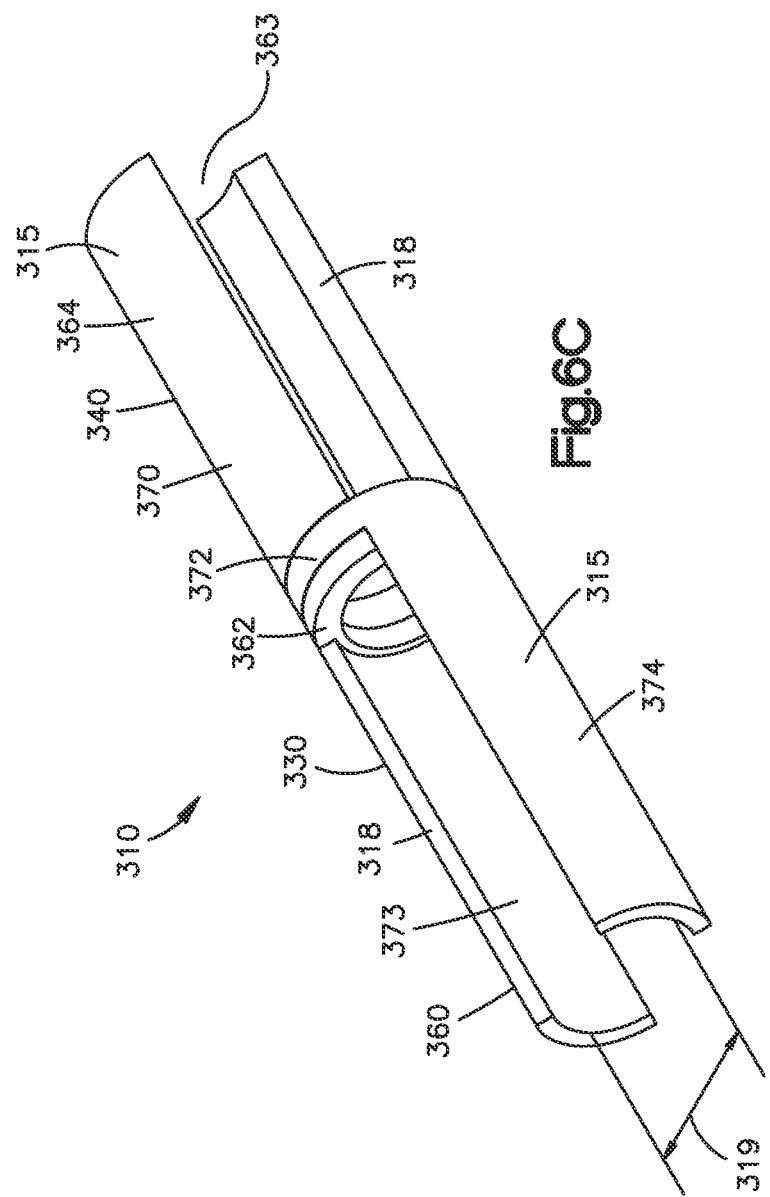

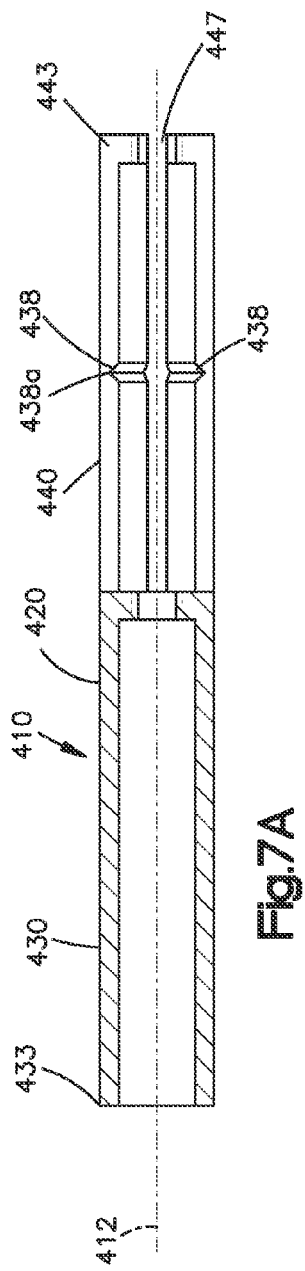
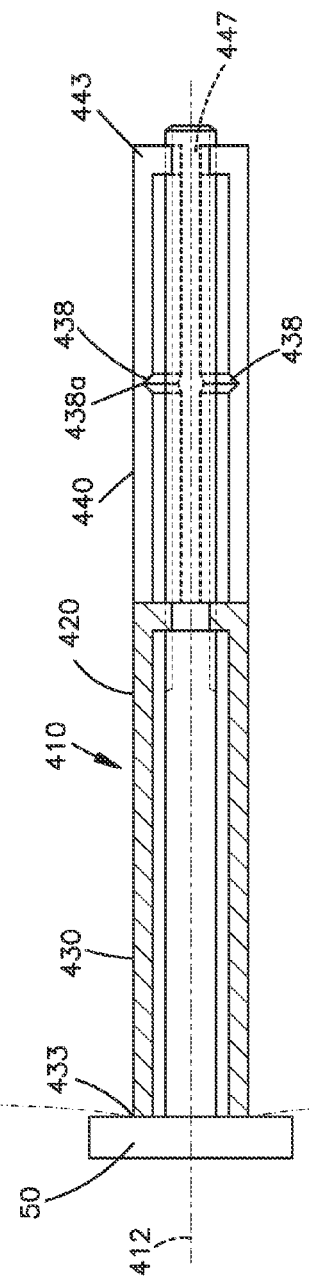

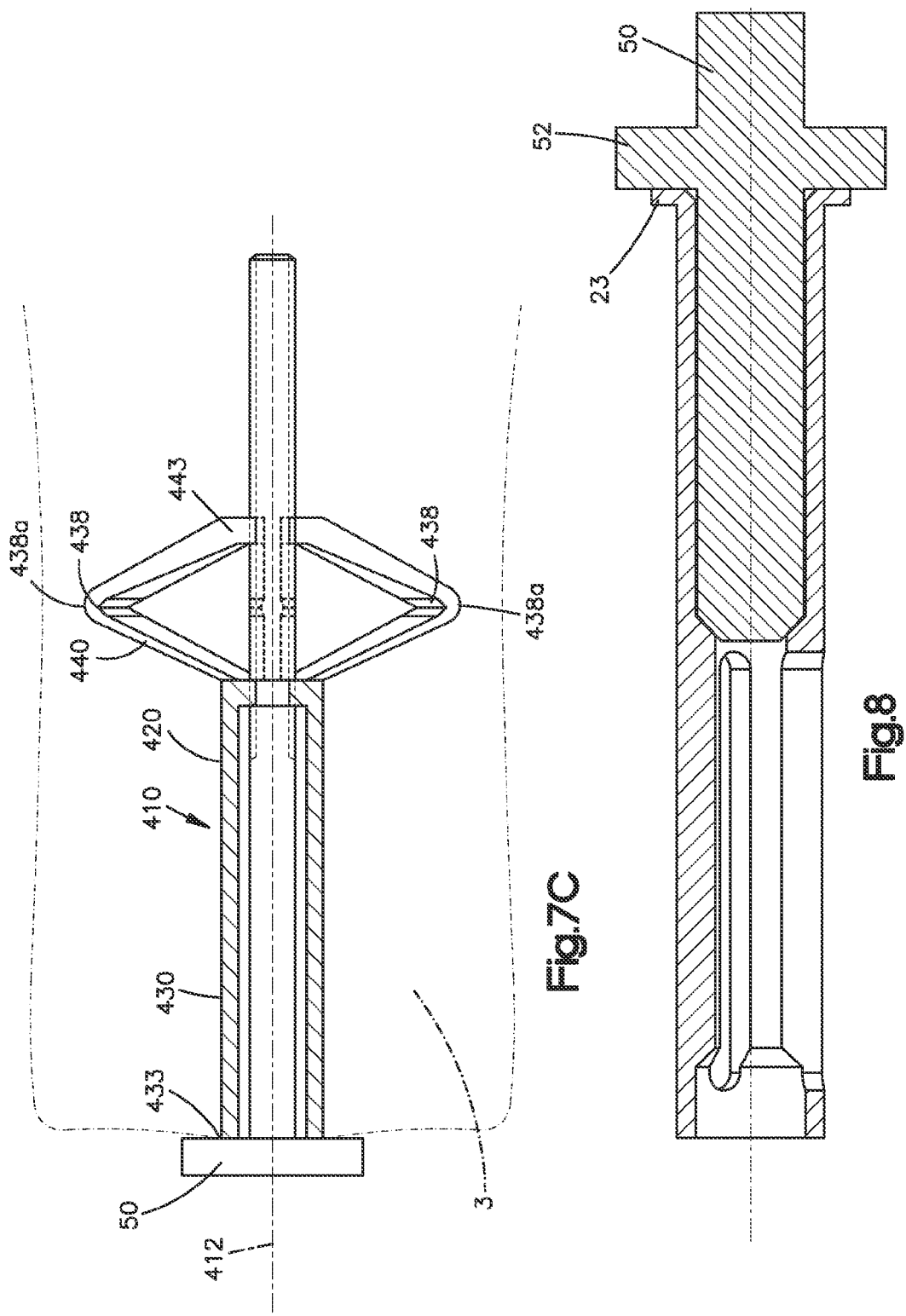

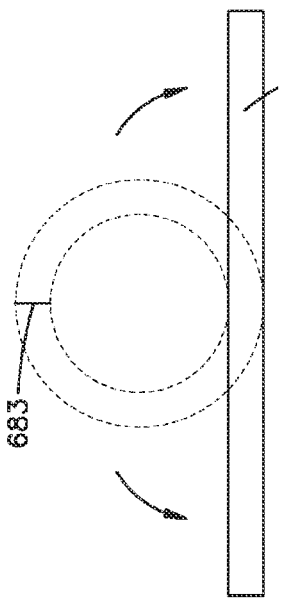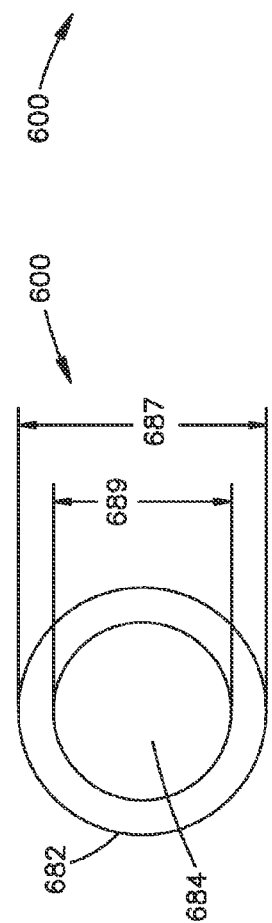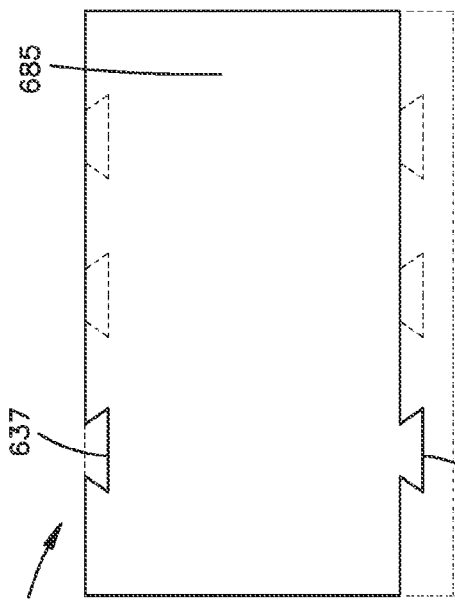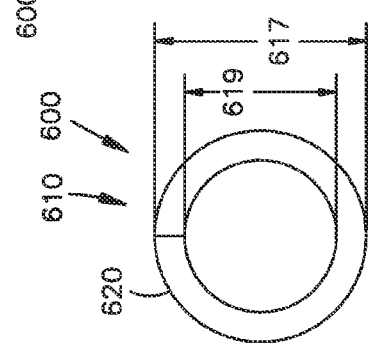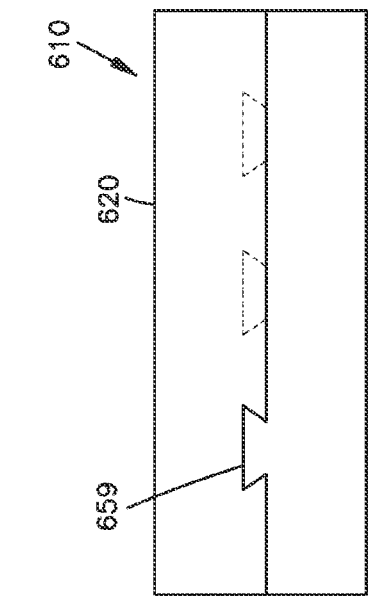

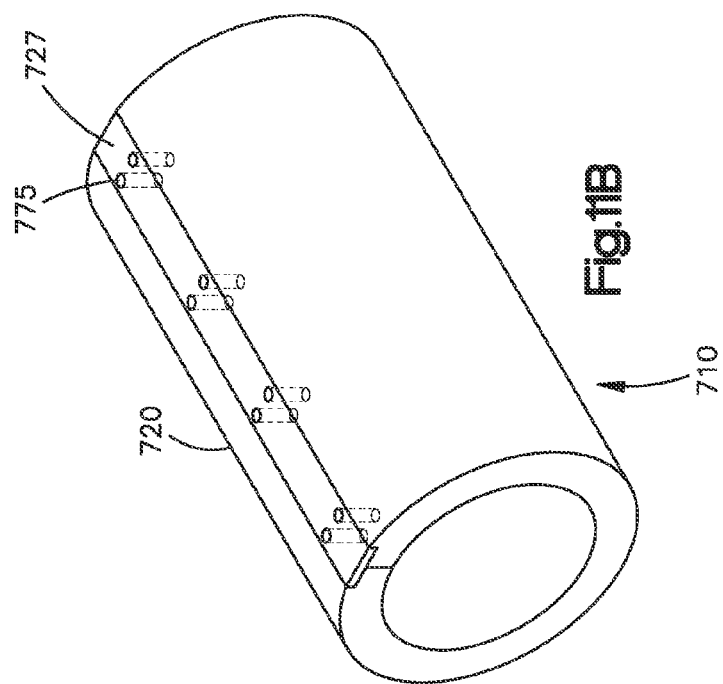
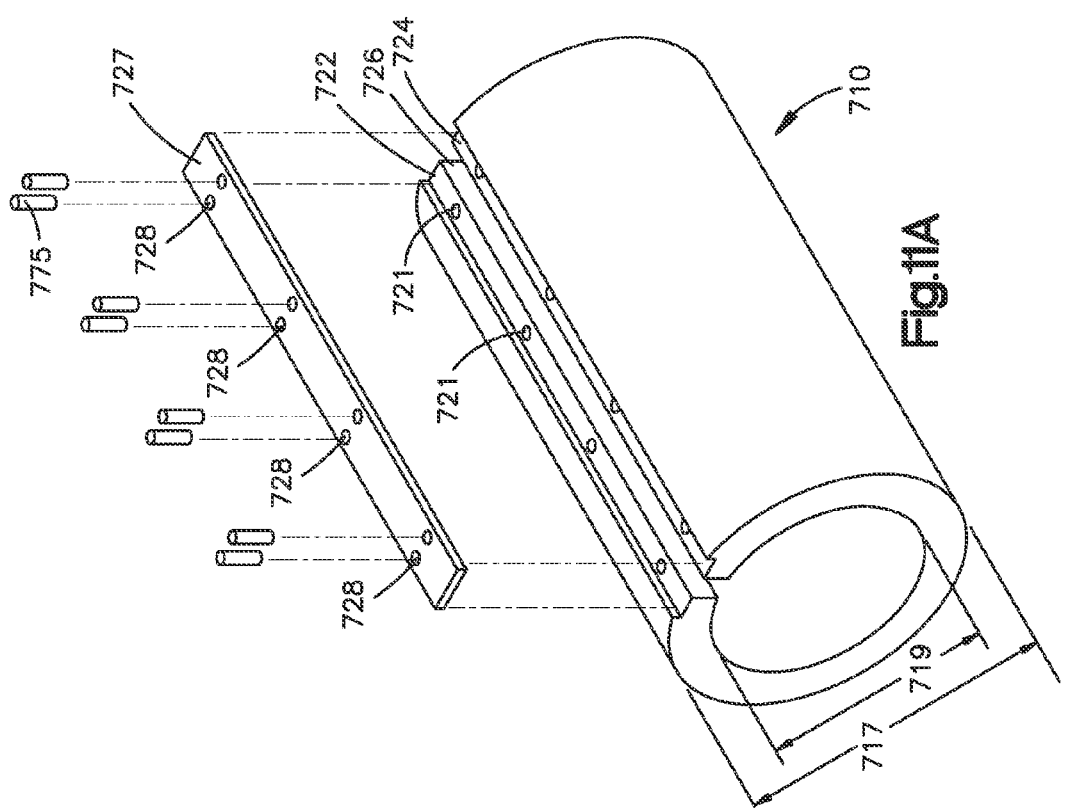
Fig.11B
Fig.11A

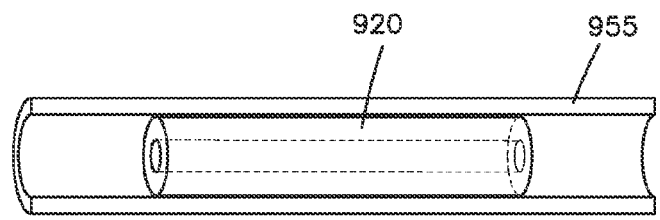
Fig.13A
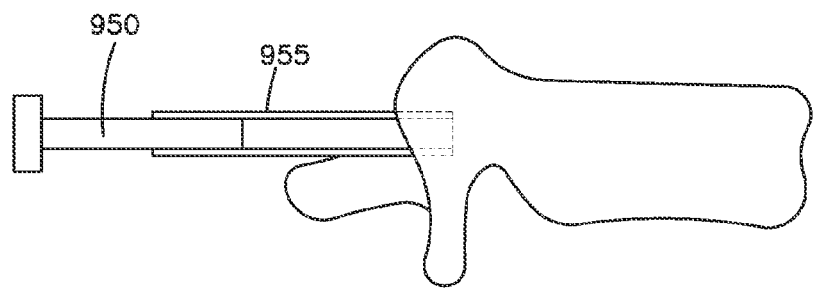
Fig.13B
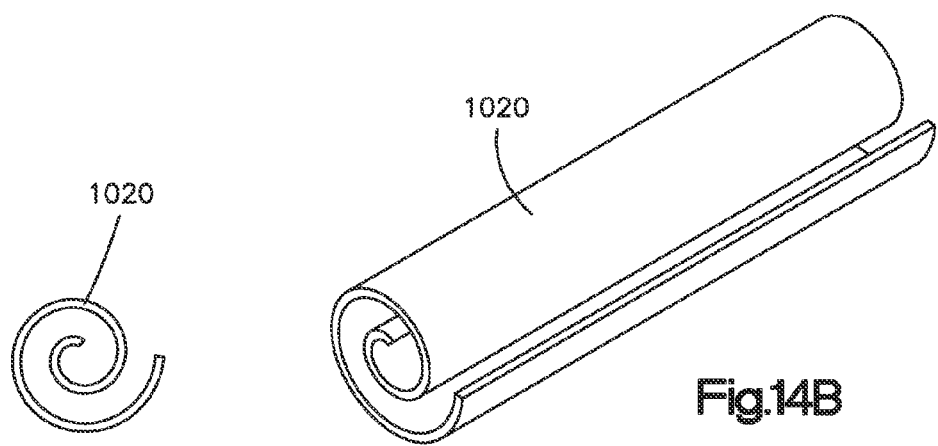
Fig.14A
Fig.14B

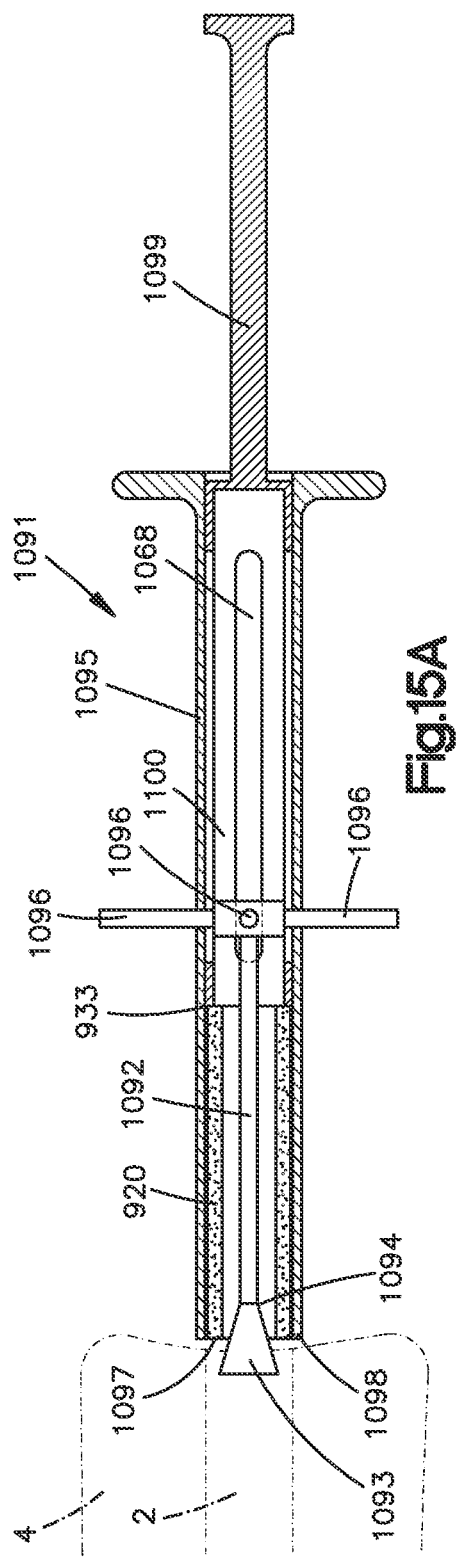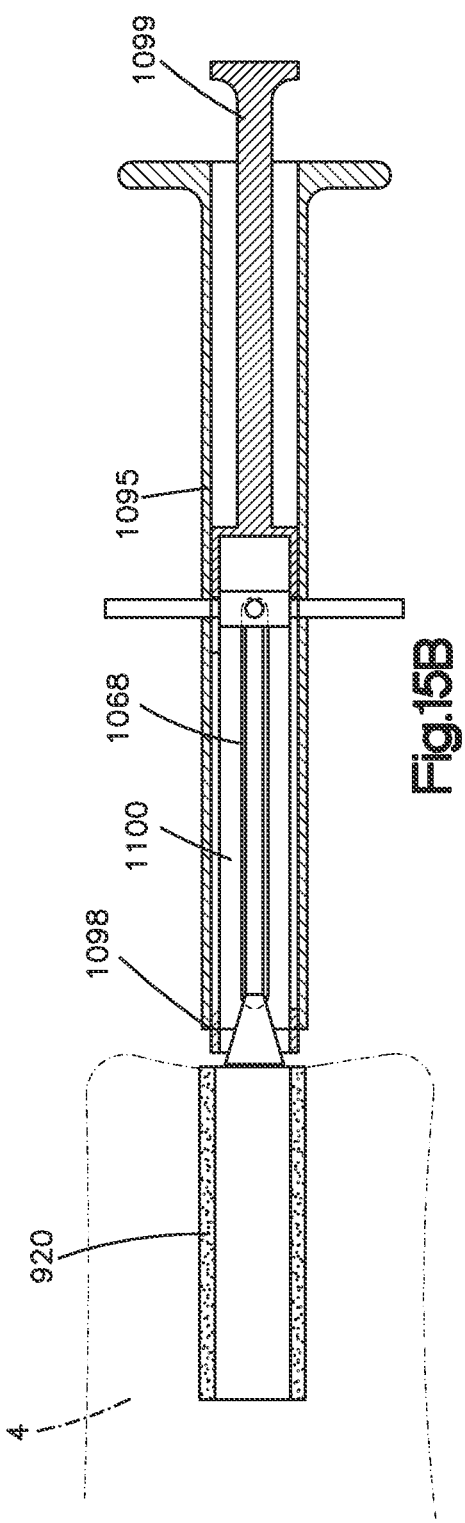

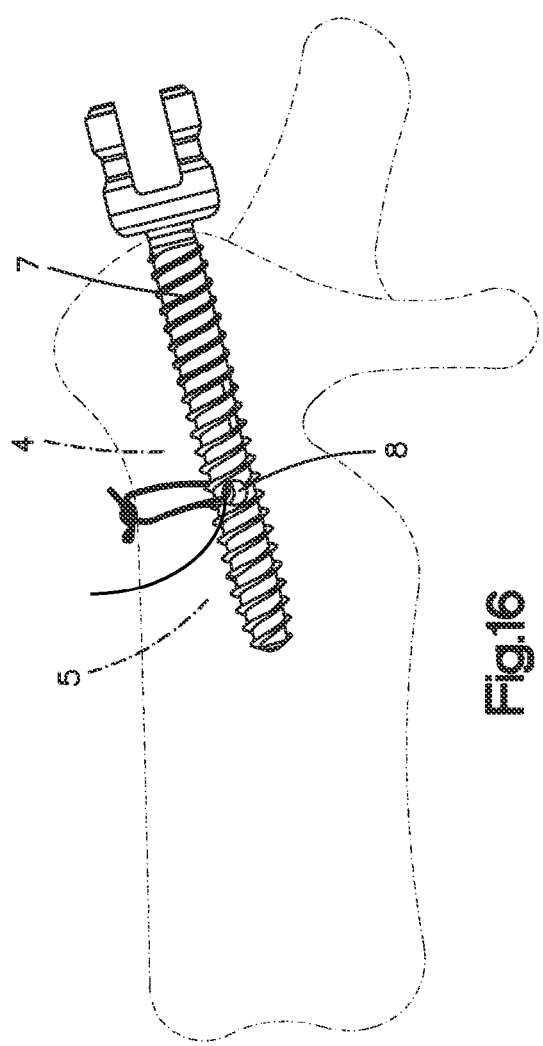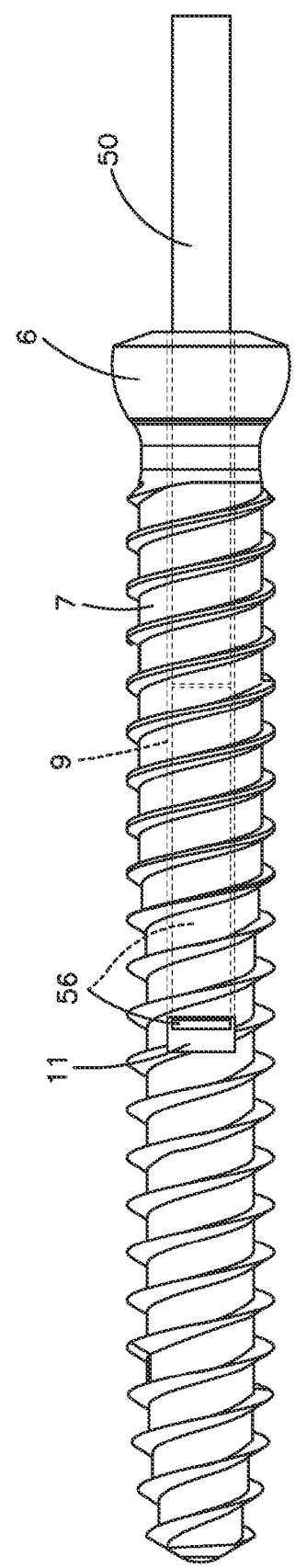
Fig.16
Fig.17

US 8,840,677 B2

ALLOGRAFT BONE PLUGS, SYSTEMS AND TECHNIQUES

CROSS REFERENCE TO RELATED APPLICATIONS

This application is a continuation-in-part of and claims priority to International Application No. PCT/US2009/048055, filed Jun. 19, 2009, entitled "Bone Screw Purchase Augmentation Implants, Systems and Techniques," which claims priority to U.S. Provisional Patent Application No. 61/073,998, filed Jun. 19, 2008, entitled "Screw Augmentation Anchor" and to U.S. Provisional Patent Application No. 61/106,862, filed Oct. 20, 2008, entitled "Pedicle Screw Purchase Augmentation Techniques and Implants." The contents of these related applications are hereby incorporated by reference in their entirety.

FIELD OF THE INVENTION

The invention relates generally to orthopedics. More specifically, the present invention relates to a device, instrumentation and method for filling bone voids and for increasing the purchase and holding strength of screws, particularly bone screws in bone, more particularly, bone screws in vertebrae.

BACKGROUND OF THE INVENTION

It is often necessary to secure a bone screw to a patient's bone. However, the presence of osteoporotic bone, fractured, damaged or diseased bone may reduce the effective purchase between a bone screw and the interior of the bone with which the screw interfaces. Further, previous screw insertion and/or an attempt at inserting a larger diameter screw may further complicate screw insertion and revision, and increase the incidence of the screw breaching the bone or the screw "stripping". In addition, prior attempts involved implanting foreign substances into the patient's bone.

In the spine it is often necessary to treat spinal disorders by, for example, securing a number of pedicle screws into the patient's vertebra and attaching elongated members, typically rods, longitudinally along a patient's spine on either side of the spinous processes of the vertebral column to the pedicle screws. One problem associated with pedicle screw fixation is loss of purchase between the bone screw and the patient's vertebrae. Another problem associated with screw fixation is loss of holding strength of a bone screw in bone, particularly a bone screw in a vertebra. Toggling of the screw in bone is another problem that may lead to loss of purchase and holding strength.

Thus there is a need for a device, instrumentation and method to reduce the complications associated with screw fixation in bone, including, but not limited to, pedicle screw fixation complications as a result of loss of purchase and/or insufficient holding strength between the pedicle screw and the vertebra. In addition, there is a need for a device, instrumentation and method to fill bone voids, such as those that are left after hardware is removed. Also, there is a need for a device instrumentation and method to improve the fit between two or more implants or instruments, for example the fit between a void and a screw or a bone dowel, more specifically that in Anterior Cruciate Ligament/Posterior Cruciate Ligament (ACL/PCL) repair procedures.

BRIEF SUMMARY OF THE INVENTION

The present invention provides a system, device, instruments and methods for improving the holding strength and purchase of a screw, preferably a screw in bone tissue, preferably in vertebral bone, for filling voids that are prepared using instruments similar to drills and the like (e.g., reamers, awls, dilators, probes, etc.), or that are left in bone tissue after hardware (e.g., pedicle screws) is removed and for improving fit between two or more instruments or implants. In one embodiment, an implant for positioning between the shaft of a bone screw, bone pin, or bone dowel and surrounding bone tissue to increase the holding strength of the screw, pin or dowel, and/or an implant for positioning in voids formed in bone is provided. The implant includes a longitudinally elongated member dimensioned and configured for insertion into a preformed hole. The member has a distal end, a proximal end, and a longitudinal axis. The implant in one embodiment may be formed as a strip, preferably a relatively thin strip preferably formed of at least partially demineralized bone, preferably allograft bone tissue that is relatively flexible, elastic and floppy, preferably at least 80% demineralized.

In another embodiment the implant may comprise an elongated member preferably formed of allograft bone tissue although alternative materials, such as, for example, PEEK, PET, PCU, PCL, EVA and other thermoplastic elastomers or other bio-compatible materials may be utilized. The elongated member may have a proximal end, a distal end, a longitudinal axis and a hollow cavity extending from a proximal opening at the proximal end toward the distal end. The member preferably has a wall forming a continuous ring shape and including a proximal portion and a distal portion. Preferably the proximal portion includes the proximal opening in communication with the cavity. The distal portion preferably includes a distal opening in communication with the cavity. At least a portion of the member preferably is at least partially demineralized, and preferably the proximal and distal portions are configured to expand. The distal portion is preferably configured to expand more than the proximal portion. The implant may be positioned within a hole formed in tissue and a screw, preferably with a shaft core diameter greater than or equal to the inner diameter of the bore, is inserted down the proximal opening of the implant.

In another embodiment, the elongated member is preferably a substantially cylindrically shaped tube or sleeve preferably having a substantially uniform outer diameter. The substantially tubular shaped member has a proximal portion having a proximal opening and a wall, and a distal portion. The outer diameter of the sleeve preferably is between about two millimeters (2 mm) and about nine millimeters (9 mm), the tube length preferably between about ten millimeters (10 mm) and about sixty millimeters (60 mm), with the distal portion preferably between about five millimeters (5 mm) and about fifty millimeters (50 mm) in length, the proximal portion preferably has a wall thickness between about three tenths of a millimeter (0.3 mm) and about one millimeter (1 mm), and the distal portion preferably has a wall thickness between about one millimeter (1 mm) and about two millimeters (2 mm). The implant optionally has one or more slots, preferably at least three (3) slots in the distal portion, wherein at least one of the slots preferably is between about ten millimeters (10 mm) and about twenty (20 mm) in length, preferably about thirteen millimeters (13 mm) in length, having a width preferably between about one millimeter (1 mm) and about two millimeters (2 mm), preferably about one and a half millimeters (1.5 mm) in width.

The wall thickness of the sleeve in the majority of the distal portion preferably is thicker than the wall thickness in a majority of the proximal portion. The distal portion may further include an optional distal end section that has a wall thickness that is thinner than its adjacent section wherein the thinner distal end section preferably overlaps with at least one of the slots, slits, cuts, grooves and perforations. The distal end section preferably may be between about one millimeter (1 mm) and about five millimeters (5 mm) in length and may form a continuous ring.

The proximal portion of the implant preferably is at least partially demineralized and demineralized to a larger extent than the distal portion. The proximal portion preferably is completely demineralized (for example, at least 80% demineralized) and the distal portion may be partially or completely demineralized. The allograft tissue sleeve may be monolithic and formed of a single piece of allograft tissue. The allograft tissue implant may be freeze-dried.

The proximal portion of the implant may optionally include at least one slot, slit, cut, groove and perforation. The at least one slot, slit, groove and perforation may form a parting line in the distal portion that preferably tears and forms expandable fingers upon insertion of a screw. In another embodiment the distal portion may have a plurality of strips connected by a continuous ring at the distal end, the strips having a thinned section that acts as a hinge and preferential fold line, whereby the continuous ring is moveable to form an expanded distal portion having folded strips.

In a different embodiment, the sleeve may include a proximal ring section, a distal ring section and a mid section wherein the proximal and distal ring sections have a continuous wall and the mid-section has a plurality of slots, slits, grooves or perforations and the mid-section is preferably thicker than the proximal and distal ring sections. The proximal and distal ring sections are configured to remain intact with relatively little expansion upon insertion of a screw down the bore while the mid-section is configured to expand, facilitated by expansion of the slots, slits, groove and perforations.

In yet another embodiment, an implant for positioning between the shaft of a screw and the surrounding bone tissue to increase the holding strength of the screw is provided, the implant having an elongated allograft tissue form dimensioned and configured for insertion into a preformed hole in bone having a distal end, a proximal end and a longitudinal axis extending therebetween. The allograft tissue form further includes an allograft tissue proximal portion and an allograft tissue distal portion. The proximal portion preferably includes a proximal opening at the proximal end, a bore forming a hollow interior and a wall surrounding the hollow interior. The distal portion preferably is solid and at least a portion of the distal portion preferably includes at least one slit. At least one of the proximal portion and the distal portion is partially demineralized and the proximal portion and the distal portion preferably are flexibly connected.

Optionally, the distal portion of the implant comprises at least one through slit forming a parting line so that the distal portion forms separable and moveable fingers that are configured to expand upon insertion of the screw. The separable and moveable fingers preferably expand more than the proximal portion.

In a still further embodiment, an allograft bone plug for positioning in bone and receiving a bone screw is provided, the bone plug having a first allograft tissue piece having a connector strip and a plurality of extremities extending from the connector strip. The connector strip forms a continuous ring connecting the extremities, and a plurality of gaps separating the extremities. The allograft bone plug has a second allograft tissue piece having a joining member and a plurality of finger members extending from the joining member. The joining member forms a continuous ring connecting the fingers, and a plurality of spaces separates the fingers. The first piece attaches to the second piece such that the connector strip is distal of the joining member while the extremities extend proximally of the joining member, and such that the fingers extend distally of the connector strip.

The second piece of the allograft bone plug preferably has a flexible connecting section that connects the fingers to the joining member wherein the flexible connecting section comprises demineralized bone. The flexible connecting section optionally includes a groove. The groove is sized and configured to retain and secure the connector strip of the first piece. The gaps separating the extremities in the allograft bone plug preferably are sized and configured to permit the fingers to fit between the extremities, while the spaces separating the fingers preferably are sized and configured to permit the extremities to fit between the fingers. The bone plug is preferably formed by sliding the first piece over the second piece with the extremities extending between the spaces. The second piece forming the bone plug optionally is thicker than the first piece.

A method for producing a tubular allograft implant configured for inserting into a previously formed hole in bone to increase the holding strength and purchase of a screw is also provided. The method includes the steps of (1) acquiring a piece of donor bone having an intramedullary canal, the donor bone characterized by an inner diameter and an outer diameter, (2) demineralizing the donor bone, (3) forming a cut through the surface of the demineralized donor bone, (4) unrolling the demineralized donor bone to form a sheet, (5) trimming the sheet to a desired set of dimensions, and (6) rolling the sheet to form a tubular implant characterized by an inner diameter that is less than the inner diameter of the donor bone and an outer diameter that is less than the outer diameter of the donor bone. The method of producing the tubular allograft implant may further comprise the step of securing the tubular implant together to prevent unrolling, for example, by bonding, welding, tacking, pinning, screwing, gluing, suturing, or the like.

A method for inserting a screw into a pedicle is also provided. The method comprising the steps of: (a) preparing a hole in the pedicle of a vertebra, (b) providing a screw for insertion into bone, (c) selecting a bone augmentation device having an outside circumference that is approximately equal to or less than the circumference of the hole formed in the vertebra, the bone augmentation device comprising a longitudinally elongated member having a proximal end, a distal end and a hollow cavity extending from a proximal opening formed at the proximal end toward the distal end, the opening in the proximal end being approximately equal to or smaller than the diameter of the screw, the elongated member having a continuous wall at the proximal end forming a ring section, (d) inserting the bone augmentation device into a vertebra so that the proximal end is substantially flush with the opening of the hole in the pedicle and the implant extends into the vertebrae, and (e) inserting the screw into the bore of the bone augmentation device.

The method may further comprise inserting the bone augmentation device, so that it resides entirely within the pedicle region. The method may further comprise selecting the bone augmentation device to be of sufficient length to extend into the vertebral body and the bone augmentation device is inserted so that the distal end resides in the vertebral body. The bone augmentation device of the method may have a proximal portion containing the proximal opening and a distal portion containing the distal end, the method further comprising the step of expanding the distal portion more than the proximal portion. The method of inserting the screw may further include expanding the distal portion of the implant in cancellous bone in the vertebral body. The method may further comprise selecting and implanting a bone augmentation device formed of at least one of allograft bone tissue, PEEK, PET, PCU, PCL and EVA. Preferably the bone augmentation device selected and implanted is formed of allograft bone tissue that is at least 80% demineralized.

A method for augmenting a bone for receiving a fastener in bone tissue is also provided. The method comprising the steps of: providing the fastener for insertion into bone; selecting a bone augmentation device having an outside circumference that is approximately equal to or less than the circumference of the hole formed in the bone, the bone augmentation device comprising a longitudinally elongated allograft tissue form having a proximal end, a distal end and a hollow cavity extending from a proximal opening formed at the proximal end toward the distal end, the opening in the proximal end being approximately equal to or smaller than the diameter of the fastener, the tissue form further having a continuous wall at the proximal end forming a ring section; inserting the bone augmentation device into the cavity so that the proximal end of the bone augmentation device is substantially inserted within the opening of the cavity and the implant extends into the cavity; and inserting the fastener into the bore of the bone augmentation device. Preferably the fastener is formed of allograft bone tissue and is at least one of a screw, a dowel, and a pin. The method may further comprise inserting the device within the opening of the cavity so that the proximal end is substantially flush with the opening of the cavity.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the device, system, kit, instrumentation and method of the present application, there are shown in the drawings preferred embodiments and techniques. It should be understood, however, that the application is not limited to the precise arrangements, structures, features, embodiments, aspects, instrumentalities and techniques shown, and that the arrangements, structures, features, embodiments, aspects, instrumentalities and techniques disclosed herein may be used singularly or in combination with other arrangements, structures, features, embodiments, aspects, instrumentalities and techniques. In the drawings:

FIGS. 4A-C illustrate side perspective views of a another preferred embodiment of a bone augmentation device in accordance with the present invention;

FIGS. 5A-C illustrate side perspective views, and an end view taken of FIG. 5A, of a preferred embodiment of a bone augmentation device in accordance with the present invention;

FIGS. 5D-F illustrate side perspective views, and an end view taken of FIG. 5D, of another embodiment of a bone augmentation device in accordance with the present invention;

FIGS. 6A-C illustrate side perspective views of a bone augmentation device in accordance with a preferred embodiment of the present invention;

FIGS. 7A-C illustrate cross-sectional views of a bone augmentation device in accordance with a preferred embodiment of the present invention and a preferred insertion instrument in accordance with the present invention;

FIG. 8 illustrates a bone augmentation device in accordance with a preferred embodiment of the present invention and a pusher preferred instrument in accordance with the present invention;

FIGS. 10A-E illustrate the steps taken during a second preferred method for forming a bone augmentation device in accordance with the present invention;

FIGS. 11A-B illustrate steps taken during a third preferred method for forming a bone augmentation device in accordance with the present invention;

FIGS. 13A-B illustrate steps taken during a first preferred method for implanting a bone augmentation device in accordance with the present invention;

FIGS. 14A-B illustrate front elevational and side perspective views of a bone augmentation device in accordance with another preferred embodiment of the present invention;

FIGS. 15A-B illustrate cross-sectional views of an inserter instrument for use during the implantation of a bone augmentation device in accordance with preferred embodiments of the present invention, such as, for example, the device of FIGS. 14A and 14B;

FIG. 16 illustrates an alternate, exemplary embodiment of a pedicle screw system in accordance with the present invention;

FIG. 17 illustrates an alternative exemplary embodiment of a pedicle screw system in accordance with the present invention;

DETAILED DESCRIPTION OF THE INVENTION

Figure 1A:
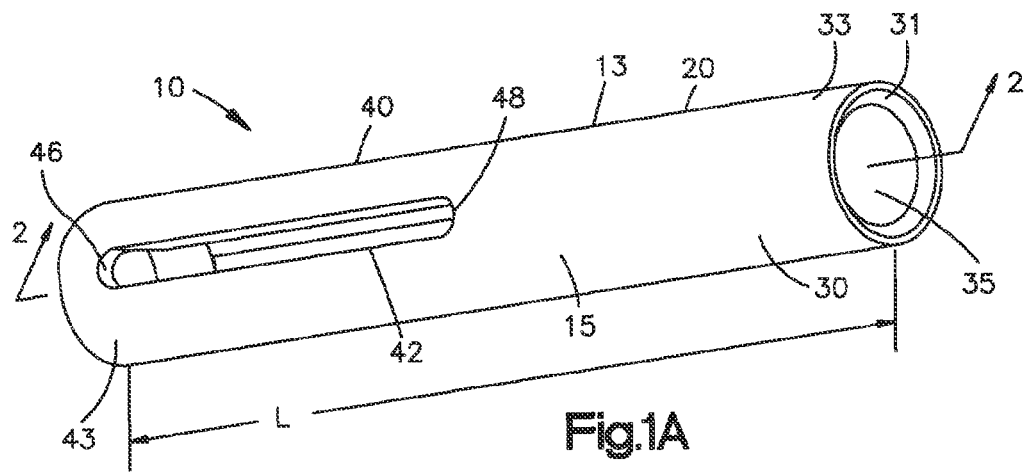
FIG. 1A illustrates a side perspective view of a bone augmentation device in accordance with a preferred embodiment of the present invention.

Certain terminology is used in the following description for convenience only and is not limiting. The words "right", "left", "lower", "upper", "top" and "bottom" designate directions in the drawings to which reference is made. The words "inwardly" and "outwardly" refer to directions toward and away from, respectively, the geometric center of the implant and designated parts thereof. The words, "anterior", "posterior", "superior", "inferior", "medial", and "lateral" and related words and/or phrases designate preferred positions and orientations in the human body to which reference is made and are not meant to be limiting. The terminology includes the above-listed words, derivatives thereof and words of similar import.

Bone implant, bone augmentation device or bone protection device 10 (also referred to as a bone plug or shim) in the form of longitudinally elongated member for positioning between shaft of a screw and surrounding bone tissue to increase the holding strength and purchase of the screw is provided. The longitudinally elongated member is dimensioned and configured for insertion into a preformed hole that is to receive the screw, the member having a proximal end, a distal end, and a longitudinal axis. The implant in one embodiment may be formed as a strip, preferably a relatively thin strip preferably formed of at least partially demineralized bone, preferably allograft bone tissue that is relatively flexible, elastic and floppy, preferably at least 80% demineralized bone. The bone augmentation device 10 may be formed of alternative materials, such as, for example, plastics including PEEK, PTU, PET, EVA, PCU or other biocompatible or bioresorbable plastics. Other materials for bone augmentation device may include metal and metal alloys, such as, for example, stainless steel, titanium or alloys thereof, ceramics and composites or other biocompatible materials now known or hereafter discovered.

Figure 1B:
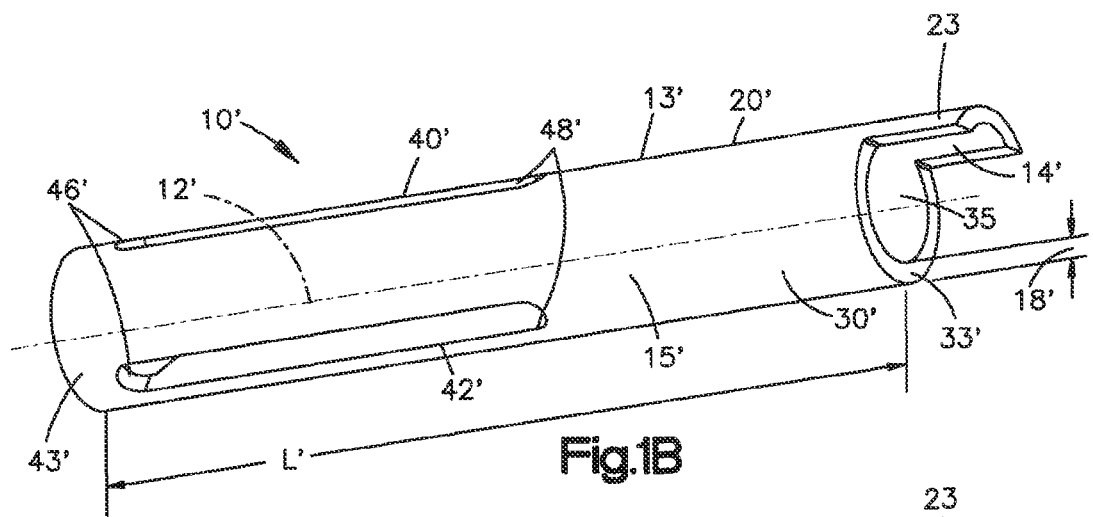
FIGS. 1B-C illustrate side perspective views of another preferred embodiment of a bone augmentation device in accordance with the present invention.
Figure 1C:
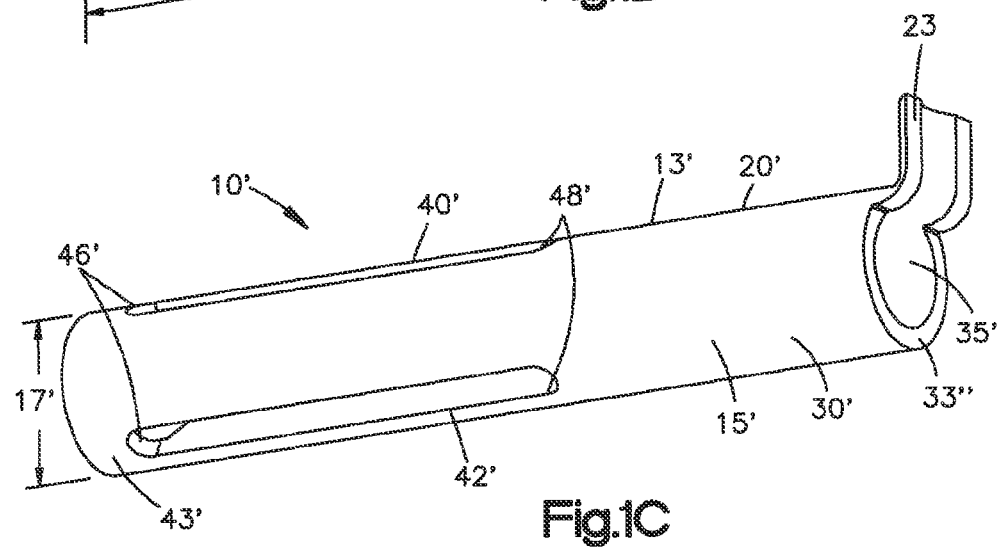
Figure 1D:
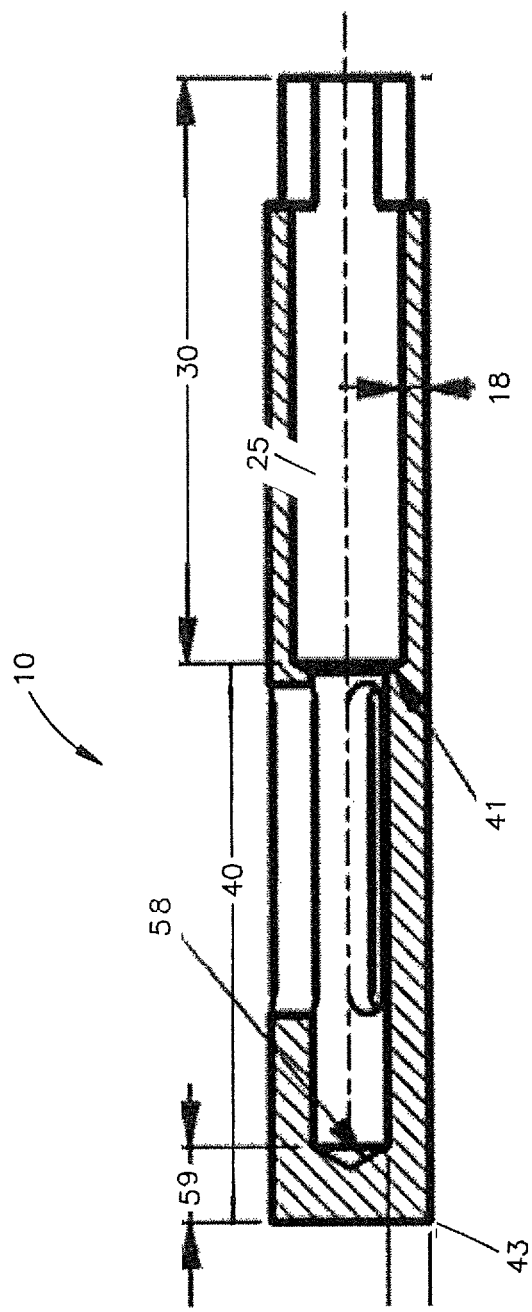
FIG. 1D illustrates a cross-sectional view of a bone augmentation device in accordance with an embodiment of the present invention, taken along a longitudinal axis.
Figure 2:
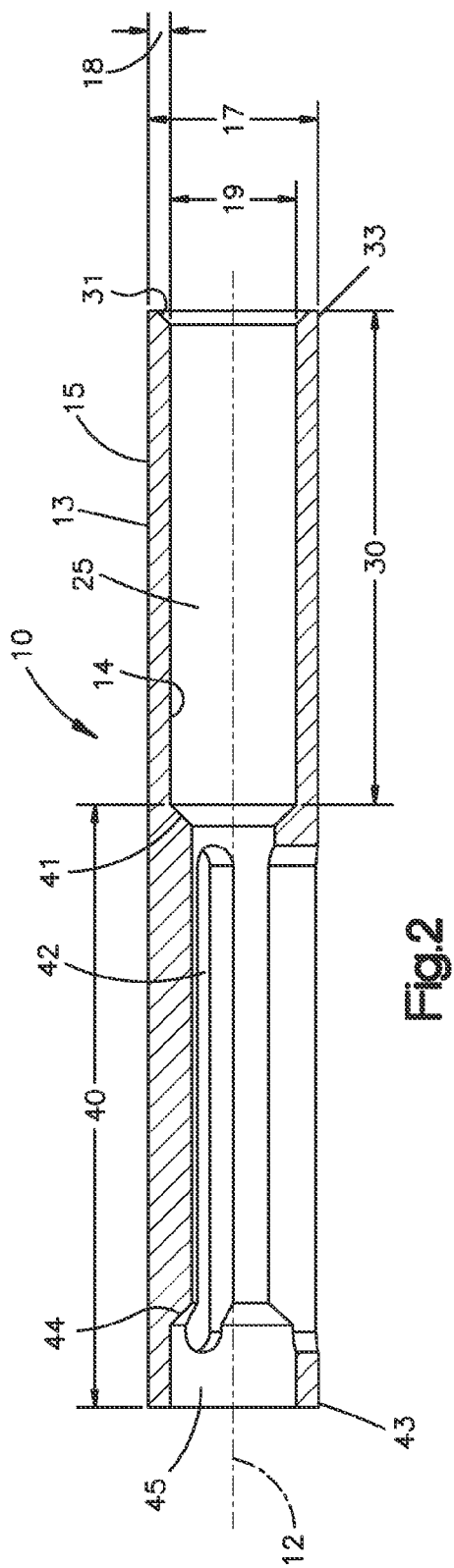
FIG. 2 illustrates a cross-sectional view of the bone augmentation device of FIG. 1, taken along line 2-2 of FIG. 1.

In another embodiment, bone plug or bone protection device 10, 10' for increasing the holding strength or purchase of a bone screw or bone plug or otherwise to protect the substrate, in this example, bone, as shown in FIGS. 1A-D and 2, may be a longitudinally elongated member preferably in the form of a tube or sleeve 20, 20' including a longitudinal axis 12, 12', a proximal portion 30, 30', a distal portion 40, 40' and a hollow central cavity, passageway or bore 25, 25'. Preferably, as shown in FIG. 2, the hollow central cavity or passageway 25, 25' extends completely through the allograft or bone plug 10, 10' from a distal end 43, 43' to a proximal end 33, 33'. The sleeve 20, 20' may be generally cylindrically shaped but may be other shapes as well. The sleeve 20, 20' preferably includes a proximal portion 30, 30' having a proximal opening 35, 35' in communication with bore 25, 25', and a distal portion 40, 40' having a distal opening 45, 45' in communication with the bore 25, 25'.

In other preferred embodiments, distal portion 40 does not have a distal opening 45 as shown in FIG. 2, but rather has a closed distal wall 58, as shown in FIG. 1D. The closed distal end can have a depth 59, thus the closed distal end can comprise a solid core, which can be advantageous, for example, when inserting the implant into bone, and can aid placement of the bone plug in voids. The depth 59 of the solid core forming the closed distal end, may vary, and in one embodiment is preferably between about one tenth of a millimeter (0.1 mm) and about seven millimeters (7 mm), as measured from the distal end 43,43' to the bore 25, 25'. The depth 59 of the closed end is preferably about seven millimeters (7 mm), and more preferably about three millimeters (3 mm). Other depths of the closed end are contemplated. A wall 15, 15' in the proximal portion 30, 30' is preferably circumferentially continuous without any openings, slots, slits, grooves or perforations therein while the wall 15, 15' in the distal portion 40, 40' optionally may contain one or more slots 42, 42', preferably about three (3) slots arranged concentrically and about one hundred twenty degrees (120°) apart around the circumference of the wall 15, 15'. The slots 42, 42' preferably extend through the wall 15, 15' and communicate with the bore 25, 25'.

It should be readily understood that the implant may include more or less slots 42' including, for example, no slots, or one, two, four, five or more slots. Slots may, for example, allow the radial expansion of the distal portion when used with a bone pin, dowel, or screw. Optionally, the proximal portion 30, 30' may also include slots, or slots 42, 42' may extend into both the proximal and distal portions 30, 30', 40, 40'. The slots 42, 42' may extend longitudinally for the majority of the length of the distal portion 40, 40'. In the exemplary embodiments of FIGS. 1A-D and 2, the slots 42, 42' in the distal portion 40, 40' may be approximately twenty millimeters (20 mm), more preferably about eighteen millimeters (18 mm) in length. The slots 42, 42' may have a width of about one millimeter (1 mm) to about two millimeters (2 mm), more preferably about one and a half millimeters (1.5 mm). Other lengths and widths for the optional slots 42, 42' are contemplated. For example, in other embodiments, the slots 42, 42' may be approximately thirteen millimeters (13 mm) in length. Preferably the slots 42, 42' do not extend to the distal end 43, 43' of the distal portion 40, 40'. Preferably, the slots 42, 42' start between about two and about two and a half millimeters (2-2.5 mm), more preferably two and two tenths millimeters (2.2 mm), from the distal end 43, 43' and extend longitudinally toward the proximal end 33, 33'. Other distances of slots 42, 42' from the distal end 43, 43' are contemplated. For example, in other embodiments, the slots 42, 42' start between about eight to about eight and a half millimeters (8-8.5 mm), more preferably about eight and two tenths millimeters (8.2 mm), from the distal end 43, 43'. Slots 42, 42' preferably have rounded ends 46, 46', and 48, 48'.

The wall 15, 15' of the sleeve 20, 20' may have a thickness 18, 18' as shown in FIG. 2 that is thinner in the proximal portion 30, 30' than in the distal portion 40, 40'. Preferably the wall 15, 15' is between about three tenths of a millimeter (0.3 mm) and about one millimeter (1 mm), more preferably about nine tenths of a millimeter (0.9 mm), thick in the proximal portion 30, 30', and preferably between about one millimeter (1 mm) and about two millimeters (2 mm), more preferably about one and sixth tenths of a millimeter (1.6 mm), thick in the distal portion 40, 40'. Portions of the wall 15, 15' in distal portion 40, 40' of the sleeve 20, 20' as will be described below may be thinner than other portions and may have a wall thickness 18, 18' approximately equal to the wall thickness 18, 18' in the proximal portion 30, 30'.

The sleeve 20, 20' may be approximately ten millimeters (10 mm) to about sixty millimeters (60 mm), more preferably about forty millimeters (40 mm) to about forty-five millimeters (45 mm) in length, although other lengths are contemplated depending upon where the augmentation device 10, 10' is to be utilized. An outer diameter 17, 17' of the sleeve 20, 20' may be substantially uniform and may be about two millimeters (2 mm) to about nine millimeters (9 mm), more preferably in one exemplary embodiment for pedicle screw fixation about six millimeters (6.0 mm) to about six and a half millimeters (6.5 mm), and in separate exemplary embodiments for bone plug applications about five millimeters (5 mm), or about six millimeters (6 mm), or about seven millimeters (7 mm). Other sizes for the outer diameter 17, 17' of sleeve 20, 20' are contemplated and will depend upon the bone screw, bone pin, or bone dowel utilized, the bone and opening being augmented, and the anatomical location of the void being treated. An inner diameter 19, 19' of the sleeve 20, 20' in the proximal portion 30, 30' is preferably about four millimeters (4.0 mm) to about seven millimeters (7.0 mm), more preferably about four and two tenths millimeters (4.2 mm) to about five millimeters (5.0 mm), and more preferably about four and four tenths millimeters (4.4 mm). Other sizes for the inner diameter 19, 19' in the proximal portion 30, 30' are contemplated depending, for example, upon the bone screw, bone pin, or bone dowel to be utilized, the opening to be augmented, and the anatomical location of the void being treated. The inner diameter 19, 19' of the proximal portion 30, 30' is preferably smaller than the diameter of the shaft of the bone screw, bone pin, or bone dowel that is intended to be utilized with the implant 10, 10'. The inner diameter 19, 19' of the sleeve 20, 20' in the distal portion 40, 40' preferably will be smaller than the inner diameter in the proximal portion 30, 30'. Preferably the inner diameter 19, 19' of the distal portion 40, 40' is about two and a half millimeters (2.5 mm) to about three and a half millimeters (3.5 mm), more preferably about three millimeters (3.0 mm).

While the implants illustrated and described herein have and will be described and may generally be used in connection with pedicle screw fixation or filling bone voids in the spine (for example, in the lumbar, thoracic or cervical regions), those skilled in the art will appreciate that the implant 10, 10' may be used in other parts of the body such as, for example, long bones, the iliac crest, and bones in the hip, wrist, hand, face, feet, ribs, mandible, extremities, cranium, etc. For example, the implants can be used in long bone applications such as ACL/PCL repair, in which a bone pin or screw may be used to keep the graft in place. The implants may be used to make the fit between the bone pin or screw and the parent bone stronger. In addition, the implant 10, 10' and variations thereof (such as sheets formed from the implant) may be used in other applications, for example as insulators, to provide covering and protection for neural elements and/or vascular structures. In these circumstances, the length, wall thickness, inner and outer diameters may be modified to meet the desired criteria of the other parts of the body, or other applications. It will further be appreciated that the implants illustrated and described herein may be used to anchor and increase the holding strength of bone screws or bone plugs in other tissue including soft tissue and have additional applications where it is desirable to increase the holding strength of screws or plugs, increase their resistance to toggling or act as a protective sheath or guard for a screw or plug to resist breaching.

The bone augmentation implant 10, 10' preferably is manufactured from bone, more preferably allograft bone. In a preferred embodiment, the implant is manufactured from cortical bone. The allograft bone augmentation implant 10, 10' preferably is at least partially demineralized. In a preferred embodiment, both the proximal and distal portions are completely demineralized, for example, but not limited to, at least 80% demineralized. In a preferred embodiment, the hardness of the implant or bone plug is similar to that of a pencil eraser. It is preferred that the allograft tissue be demineralized in the proximal portion so that the proximal portion of the bone implant is relatively flexible, elastic and floppy. The bone tissue may be demineralized by submerging in a hydrochloric acid bath at a concentration of ~0.3N for a period of between about half an hour (0.5 hr) to about twenty four hours (24 hr), preferably about six hours (6 hr) to about eight hours (8 hr). Since the extent of demineralization in an acid bath depends upon the shape and thickness of the bone tissue, the time of submersion, the environmental conditions and the concentration of the acid bath, the time of demineralization for particular implants will vary. Where both the proximal and distal portions are completely demineralized, or demineralized to the same extent, the distal portion may be more rigid by having thicker walls 15, 15' in the distal portion or by other means. The additional rigidity preferably provides resistance to pull out due to wedging of the distal portion between the screw and the vertebrae. Alternatively, the proximal portion 30, 30' of the allograft sleeve 20, 20' is completely demineralized (for example, at least 80% demineralized) and the distal portion 40, 40' is partially demineralized or nondemineralized, such that the proximal portion 30, 30' assumes a softer characteristic than the distal portion 40, 40'.

Since the implants are highly demineralized, they can be easily cut into pieces for use in spaces where the voids are smaller than the implant. Highly demineralized implants can be cut along the length of the implant to make sheets appropriate to fill in areas such as the iliac crest, or to reduce stress risers under the anatomical plates used for bony fusions, etc. The sheets can be modified to create tubes of other (smaller) dimensions. In addition, the implants can be machined to have a rough outer surface (e.g., ridges, high points, knurl pattern, etc.) in order to increase friction and improve pull-out resistance. In general, due to the flexible, conformable, and deformable nature of the implants, they can be used to effect a better or tighter fit between two mating parts in any surgery.

The sleeve 20, 20', may be constructed such that both the proximal portion 30, 30' and distal portion 40, 40' are formed monolithically from the same single piece of allograft bone tissue. Alternatively, the proximal portion 30, 30' may be separately formed from the distal portion 40, 40' and thereafter coupled together, preferably by allograft bone tissue and without adhesive, although adhesive may be employed.

The implant or bone plug 10, 10' may be used for pedicle screw applications and may be supplied in different diameters for different size pedicle screws, for example five, six and/or seven millimeter (5, 6 and/or 7 mm) pedicle screws. The implant 10, 10' may be between about ten millimeters (10 mm) and about sixty millimeters (60 mm) in length L, preferably approximately forty millimeters (40 mm) in length with an approximately twenty millimeter (20 mm) proximal portion 30, 30' and an approximately twenty millimeter (20 mm) distal portion 40, 40'. The bone augmentation implant 10, 10' is preferably inserted into a pedicle 4 of a vertebra 3 such that the proximal portion 30, 30' is located in the pedicle region where the bone is primarily cortical bone, and preferably the distal portion 40, 40' extends into and is located in the vertebral body 5 where the bone is primarily cancellous bone. Other lengths of the implant 10, 10' may be utilized, and different proximal and distal length portions may be utilized so that different size vertebrae 3 may be treated.

The proximal portion 30, 30' is preferably completely demineralized so that it is soft, flexible, elastic and floppy. The proximal portion 30, 30' is also preferably thin so that the pedicle screw, upon insertion into and through the proximal portion 30, 30' presses the sleeve 20, 20' into the wall of the pedicle 4 to provide increased purchase and anchoring of the bone screw without putting undue stress on the pedicle wall. Preferably no or minimal axial force is exerted on the implant as the screw is inserted and preferably the implant, in at least the proximal portion, may act as a protective sheath that may protect neural elements from the screw after a pedicle breach by the pedicle screw. As the screw is rotated, the first few threads bite into the soft allograft bone plug, fixing the proximal portion of the bone plug in the wall of the pedicle 4. Preferably, any potential motion of the bone plug in the direction of screw insertion is resisted and/or avoided by the initial fixing of the proximal end in the pedicle.

In the second preferred embodiment, the bone implant 10' includes a protrusion 23 (shown in FIGS. 1B-D and in FIG. 8), such as a lip or tab at the proximal end 33'. The tab or protrusion 23 preferably results in an extension, shoulder or flange beyond the outer diameter of the proximal portion 30', such that the tab 23 restricts the implant from rotating and/or translating distally (e.g., into the vertebra 3) as the bone screw, bone pin, or other graft is inserted. The tab 23 may thus serve as a visual aid during placement of the implant, for example to confirm that the implant is not being pushed too deep inside the bone cavity or void. The tab 23 may assume the form of a full cylindrical section, a partial section or a small tab. The tab may extend a length of about five millimeters (5 mm) away from the proximal end 33, 33' and may have a thickness of about one to one and a half millimeters (1-1.5 mm), more preferably one and three tenths millimeters (1.3 mm). Other tab lengths and thicknesses are contemplated.

In the second preferred embodiment, the tab 23 shown in FIGS. 1B-1C is provided on sleeve 20'. The tab 23 is manufactured in a straight condition, as shown, for example, in FIG. 1B, as a monolithic extension of the allograft bone tissue of the sleeve 20'. Since the material is preferably demineralized allograft bone, the tab 23 is preferably flexible. Before implantation of the screw 7, the screw sleeve 20 is positioned in the prepared hole and the tab portion 23 is bent (FIG. 1C), possibly with a holding sleeve, or forceps, such that the bent tab 23 rests on the outer portion of the pedicle 4. Either a holding sleeve-like instrument, forceps, or an awl-like instrument may be used to pin the tab 23 down lightly to the outer wall of the pedicle 4. Once the sleeve 20' is in place and secured using the tab 23, the pedicle screw is implanted. The tab 23 preferably resists any inward motion of the sleeve 20' into the pedicle hole as a result of the motion of the screw 7 in that direction. The tab 23 preferably provides a visual indicator for the surgeon that the allograft or bone plug is correctly positioned in the pedicle 4 and has not moved axially with the screw 7.

In the preferred embodiments, the distal portion 40, 40' of the implant 10, 10' is preferably thicker than the proximal portion 30, 30' so that as the pedicle screw 7 extends into the distal portion 40, 40', the distal portion 40, 40' expands in the cancellous portion of the vertebral body 5 to perform a wedging function of the implant 10, 10' in the bone. The pedicle screw 7 preferably extends into the distal portion 40, 40', may extend the length of the distal portion 40, 40', and may extend out the distal end 43, 43' of the implant 10, 10'. Alternatively, the implant may be of a length so that the distal portion is located entirely in the pedicle 4 and does not extend into the cancellous portion of the vertebral body 5.

In the embodiments where the implant is of sufficient length to extend into the vertebral body, the distal portion 40, 40' preferably expands more than the proximal portion 30, 30', particularly in the cancellous bone, and preferably would expand to a size that is larger than the opening in the pedicle region 4 where the proximal portion 30, 30' is located to resist the implant 10, 10' and pedicle screw 7 from pulling out of the vertebra 3. The distal portion 40, 40' may optionally include slots (i.e., material removed from the implant) or slits (i.e., cuts in the wall) to facilitate the expansion of the distal portion 40 to assist in the wedging of the implant into the vertebral bone. The slots 42, 42' or slits may extend completely or partially through wall 15, and may be on the interior or exterior surfaces of the wall 15, 15'. The slots or slits may take the form of grooves that do not extend through the full thickness of the wall 15, 15', or perforations or other features in the wall 15, 15' to increase the flexibility of the implant or implant 10, 10' and its ability to expand.

In the preferred embodiments, the distal portion 40, 40' undergoes substantially uniform expansion or bulging, and preferably substantially uniform expansion or bulging in the middle of the distal portion. To facilitate substantially uniform bulging or expansion of the distal portion, the distal end 43, 43' of the sleeve 20, 20' may be thinner than its adjacent portion, and preferably substantially all the remaining portion of the distal portion 40, 40'. That is, the sleeve wall 15, 15' is thinned out at the distal end 43, 43' compared to its adjacent section. Preferably, the distal end 43, 43' has a wall thickness 18, 18' of between about a half of a millimeter (0.5 mm) and about one millimeter (1 mm), preferably about nine tenths of a millimeter (0.9 mm). The distal end section 43, 43' preferably has a wall thickness 18, 18' about equal to the wall thickness of the proximal portion 30, 30'. The distal end section 43, 43' may be approximately three millimeters (3 mm) in length and preferably overlaps, as shown in FIG. 2, with the optional slots, slits and/or grooves 42, 42' formed in the distal portion 40, 40' of the sleeve 20, 20'. In the first and second preferred embodiments there is a transition 44, 44' from the thicker distal portion 40, 40' to the thinner distal end section 43, 43', more preferably the wall thickness 18, 18' transitions at an angle of about forty-five degrees (45°) to about seventy degrees (70°), more preferably about sixty degrees (60°). A further transition or internal step 41, 41' in wall thickness 18, 18' preferably may occur between the thinner proximal portion 30, 30' and the thicker distal portion 40, 40', and the wall thickness may transition at about a forty-five degree (45°) to about seventy degree (70°) angle, more preferably about a sixty degree (60°) angle. Other angles and locations for the wall thickness transition are contemplated, as are multiple transitions in wall thickness 18, 18'.

Referring to FIGS. 1A-D and 2, the sleeve 20, 20' is useful as a bone augmentation device or bone plug 10, 10', or as part of a system for pedicle screw fixation, particularly for augmenting pedicle screw insertion and anchoring in a vertebra 3. The sleeve 20, 20' is intended to increase the purchase or holding strength of the pedicle screw 7 in the vertebra 3, and may find particular application in osteoporotic bone. The bone augmentation device may also be used to avoid the need to use a larger diameter screw in revision surgery, or to improve purchase of the largest diameter screw appropriate for the bone and given surgical procedure. In use, an opening or bore is formed in the pedicle 4 of a vertebra 3 that corresponds roughly to the outside diameter of the pedicle screw 7 to be inserted into the vertebra 3. The opening, hole or bore in the bone can be formed by methods now known or later discovered, such as, for example the use of drill bits, trocars, series of dilators of increasing outer diameter, etc. An appropriate sized implant 10 is provided and selected for insertion into the opening in the bone. The implant 10 is selected based upon the size of the pedicle screw 7 to be utilized, and preferably has an inner diameter 19, 19' in the proximal portion 30, 30' and distal portion 40, 40' that is approximately equal to, or less than, the diameter of the shaft of the pedicle screw 7. The implant 10, 10' is also selected to have an appropriate length, and preferably has a length so that the pedicle screw 7 extends into the distal portion 40, 40' of the sleeve, preferably through the majority of the distal portion 40, 40' and more preferably through substantially the entire length of the sleeve 20, 20'. The length of the sleeve preferably is selected to extend into the vertebral body 5 where the cancellous bone is located, but alternatively the sleeve may be entirely located within the pedicle 4 of the vertebrae. In one example, the pedicle screw 7 may have a forty-millimeter (40 mm) shaft and the sleeve may be approximately forty millimeters (40 mm). Other length screws 7 and sleeves 20, 20' are contemplated.

The selected implant 10, 10' is inserted into the opening formed in the bone so that the proximal end 33, 33' of the proximal portion 30, 30' is substantially flush or even with the start of the opening formed in the bone, and the distal portion 40, 40' is located within the bone and preferably extends into the cancellous region of the vertebral body 5. The pedicle screw 7 is inserted into the sleeve 20, 20' by screwing, i.e., rotating, the screw 7 so that the distal end of the screw 7 extends and travels through the proximal portion 30 of the sleeve 20, 20'. As the screw 7 moves through the proximal portion 30, 30' of the sleeve 20, 20', the sleeve 20, 20' preferably expands and presses into the wall of the pedicle 4 surrounding the opening in the bone so that an interference fit is formed between the sleeve wall 15, 15' and the bone. As the screw 7 is further inserted into the sleeve 20, 20' the distal end of the pedicle screw 7 enters the thicker distal portion 40, 40' of the sleeve 20, 20', and expands the distal portion 40, 40' of the sleeve 20, 20' preferably into the cancellous bone of the vertebral body 5. The distal portion 40, 40' preferably expands more than the proximal portion 30, 30', and preferably expands to a larger size than the opening in the proximal portion or pedicle area 4 of the bone, and more preferably creates a wedging effect in the bone, more preferably a bulging effect in the distal portion 40, 40' that acts as a plug to assist in increasing the holding strength of the bone screw in bone. As the screw 7 is inserted into and down the sleeve 20, 20', the sleeve 20, 20' preferably does not move axially down the hole in the direction of the screw.

In use, the distal portion 40, 40' of the sleeve 20, 20' may sever as it expands so that the distal end section 43, 43' rips at the distal ends of the slots 42, 42'. In use, the area of the distal end section 43, 43' between the slots 42, 42' and the opening 45, 45' may rip or tear in a longitudinal manner to permit further expansion of the distal portion 40, 40' and may preferably separate the distal portion into one or more fingers. The thinned section of the distal section 43, 43' preferably facilitates the uniform and symmetric bulging and expansion of the distal portion 40, 40' and may facilitate ripping of the distal section 43, 43' between the opening 45, 45' and the distal end 46, 46' of one or more of the slots 42, 42' to create multiple fingers. This ripping or breakage of the implant 10, 10' in the distal end portion 43, 43' adjacent to multiple slots 42, 42' preferably facilitates the formation of fingers and a more uniform and symmetric bending, bulging and expansion than if the distal section remained as thick as the thicker portions of the distal portion 40, 40'.

The proximal portion 30 optionally may include a plurality of longitudinal slots, slits grooves or perforations (not shown) along the longitudinal axis that terminate just prior to the proximal end 33, 33' of the sleeve 20, 20'. For example, the slots or slits may be formed from the external wall surface 13, 13' of the proximal portion 30, 30' all the way through to the hollow interior wall 14, 14' of the proximal portion 30, 30'. The slits alternatively extend radially from the external wall surface 13, 13' but terminate prior to reaching the hollow interior wall 14, 14' of the proximal portion 30, 30'. The slits also may extend from the interior wall 14, 14' radially toward the exterior wall 13, 13' but terminate or stop prior to reaching the exterior wall 13, 13' of the proximal portion 30, 30'. The slits or slots may also take on the form of perforations that include a series or plurality of punctures that penetrate or partially penetrate the wall 15, 15' that may be aligned in a pattern or are randomly formed in the wall 15, 15'.

The implant or bone plug 10, 10' may also be used for bone plug applications, to fill voids in bone, including those in long bones, the iliac crest, and spine, that are prepared or that are left after removal of hardware (e.g., pedicle screws). The implants can be used, for example, to backfill voids created by removal of hardware from load bearing bones, such as heel or ankle bones where bony voids can create stress risers. In other embodiments, the voids can be created, for example, using instrumentation such as general surgical dilators and bone tamps, or drills, reamers, awls, dilators, probes, etc. For hard bone, smaller dilators or tamps are preferably used to start, with progressively larger diameter instruments used to create a void of the desired size. In these bone plug applications, the implant embodiments described herein can be used alone or in combination with other allografts or autografts (e.g., bone pins or bone dowels) instead of pedicle screws. Accordingly, as used herein, pedicle screw 7 may be a bone screw, bone pin, bone dowel, or the like.

In an exemplary method for use with a bone pin or bone dowel, the implant is placed in the void, with the proximal tab remaining outside the void. The proximal tab is held, using forceps or similar instruments to act as a counterforce to stop rotation or axial motion of the implant with the bone screw, bone pin, or bone dowel, and the bone screw, pin, or dowel is slowly inserted. The proximal tab preferably is held until at least half the length of the bone screw, pin, or dowel is inserted through the implant.

The bone implants or plugs can be used freeze dried or wet. In certain preferred embodiments, the implant may be freeze dried or lyophilized. In its freeze dried form, the implant preferably has a smaller outside diameter compared to its fully reconstituted state. Therefore, it can be inserted freeze dried inside a smaller void or cavity than would be accessible by a non-freeze dried implant, and can be allowed to reconstitute with blood, in situ. As the implant reconstitutes, it regains its original dimensions. In freeze-dried and/or ready-to-use form, the implant may appear bent, crooked, small and/or have white coloring on the inside or outside walls; however, the implant will be restored to normal condition after sufficient rehydration. When fully rehydrated, the proximal portion of the implant can be stretched radially, to about a 32% increase in diameter, relative to the dry diameter. To rehydrate, the implant may, for example, be submerged in a sterile bath of saline. At temperatures of about 100-110° F., the implant may be ready for use in about 5-6 minutes, and fully rehydrated in about 10 minutes or more. Where the saline bath is at temperatures of about 60-70° F., the implant may be ready for use in about 10-12 minutes, and fully rehydrated in about 15 minutes or more. The implant may be considered sufficiently rehydrated if the proximal tab can be bent and an appropriate size instrument (e.g., general surgical dilator and bone tamp) can be inserted into the implant until the instrument tip touches the step inside the implant. The implant may also be considered sufficiently rehydrated if, when pressure is applied to outer diameter of the proximal or distal section of the implant, the inner walls of the implant can be made to touch each other without any damage to the implant. The implant can have multiple holes in its side walls for quick reconstitution. Because the implant is very deformable, it can adjust its dimensions to make a better fit in the cavity or void it is inserted into.

In certain embodiments, the closed distal portion of the bone plug can have a small hole at the distal end, in communication with the bore, to accommodate a guide wire, so that the implant can slide over the guide wire to a desired location. This guide wire hole permits the implant to be used in minimally invasive surgical procedures. Cannulated dilators, or other instruments such as forceps, may also be used to hold or place the bone plug.

In other embodiments, an instrument with a substantially cylindrical shape, such as a general surgical dilator, can be used to insert the implant into the surgical location. The dilator can be inserted fully or partially into the bore of the implant, and can rest against the implant, such that the implant stays on the dilator without falling off until it is implanted. For example, the instrument can rest against the closed distal end 43 or the internal step 41 in order to generate the force necessary to overcome any friction. The implant and dilator are thus inserted into the bone void and, once the implant is in position, the dilator is pulled out of the implant, while holding the implant in place, for example, via the proximal ring or tab. The implant is thus inserted such that more force is borne by the distal end than the proximal end.

Many of the methods and features described in reference to implant 10 of FIGS. 1A-D and 2 will also apply to the other embodiments described and illustrated herein, particularly the embodiments of FIGS. 3-14. FIGS. 3A-D illustrates a different preferred embodiment of a bone augmentation or bone plug device. The bone augmentation device 110 of FIG. 3 is preferably formed from completely or partially demineralized allograft bone tissue and preferably forms an approximately cylindrical tube or sleeve 120 having a longitudinal axis 112. The bone augmentation device 120 has a proximal portion 130 and a distal portion 140. The proximal portion 130 preferably is formed of completely demineralized bone (e.g., at least 80% demineralized) and has a hollow cavity or passageway 125 in communication with proximal opening 135. An inside diameter 119 of the hollow portion preferably is substantially the same as or slightly smaller than the diameter of the bone screw, pin, or dowel intended to be inserted into and through the bone augmentation device 110. The proximal portion 130 and distal portion 140 of the bone augmentation device 110 preferably is completely demineralized, (e.g., at least 80% demineralized. Alternatively, the proximal portion 130 of the augmentation device 110 may be completely demineralized and the distal portion 140 may be partially demineralized or non-demineralized such that the proximal portion 130 is softer and more flexible than the distal portion 140.

The proximal portion 130 preferably includes a plurality of slits, slots, grooves or perforations 136, similar to the slits, slots, grooves or perforations 42, formed along the longitudinal axis 112 that terminate just prior to the proximal end 133 of the implant. The implant 110 of FIG. 3 is shown with six (6) slits 136, although more or less slits may be employed as desirable. The slits 136 may extend partially or entirely through the wall 115 of the implant 110, although the slits 136 in the preferred embodiment of FIG. 3 extend only partially through the wall 115 from the exterior surface 113 of the sleeve 120 toward the internal wall surface 114. The proximal portion 130 may have the wall thickness 18, outer and inner diameters 17, 19 and length as described above for the embodiments of FIGS. 1A-D and 2. The total length L3 of the sleeve 120, and the lengths of the proximal portion 130 and distal portion 140 may have the same lengths as discussed above for the embodiments of FIGS. 1A-D and 2.

The distal portion 140 of the allograft implant 110 of the embodiment of FIG. 3 is preferably solid and may be flexibly connected to the proximal portion 130. The distal portion 140 preferably includes one or more slits 147 that preferably extend all the way from one side of the distal portion to the opposite side of the distal portion. In the embodiment of FIG. 3, two through-slits 147 are disposed ninety degrees (90°) apart along the distal portion 140 such that each end of a through slit 147 is disposed ninety degrees (90°) apart from the next through slit 147 to form a cross-hairs pattern. While the distal portion 140 of the embodiment of FIG. 3 has been shown with two through slits forming four expandable fingers 147a flexibly connected to the proximal portion 130, it can be appreciated that more or less through slits 147 may be included in different orientations, lengths, and depths in the distal portion 140 to form more or less expandable fingers 147a flexibly connected to the proximal portion. Alternatively, the distal portion 140 may also have a hollow cavity preferably with a cannulation that is smaller in diameter than the cannulation that characterizes the proximal portion 130. In addition, the diameter of the cannulation in the distal portion 140 may be approximately the same as the diameter of the cannulation in the proximal portion 130. This alternative embodiment having the cannulated distal portion would be similar to FIGS. 5D-F. The interior of the cannulated proximal and/or distal portions 130, 140 may also be demineralized, for example to assist in the bite-in of the pedicle screw 7.

The distal end 143 of the implant 110 of the third preferred embodiment may include a point or blunt end 143a for ease of insertion. Preferably, the external surface 113 of the proximal and/or distal portion 130, 140 of the sleeve 120 may include surface texturing to improve the grip between the allograft implant 110 and the surrounding bone. In one embodiment, the distal end of the proximal portion 130 may optionally include a beveled edge 131 (see edge 31 in FIG. 1) such that an insertion instrument, such as a plunger or push rod, can come to bear against proximal end 133 of the proximal portion 130 during the insertion of the implant 110 into the vertebrae 3. The beveled edge 131 can also act as a lead in chamfer 131 to locate the pedicle screw 7 and assist in starting the pedicle screw. Further, both the proximal portion 130 and the distal portion 140 may be formed monolithically from the same allograft tissue form. The proximal and distal portions alternatively may be machined from separate allograft bone pieces, and thereafter coupled together to permit movement between the pieces, preferably flexibly connected by allograft bone pieces, as will be described in greater detail below. Adhesive may or may not be used as desired to connect the portions together.

Figure 3A:
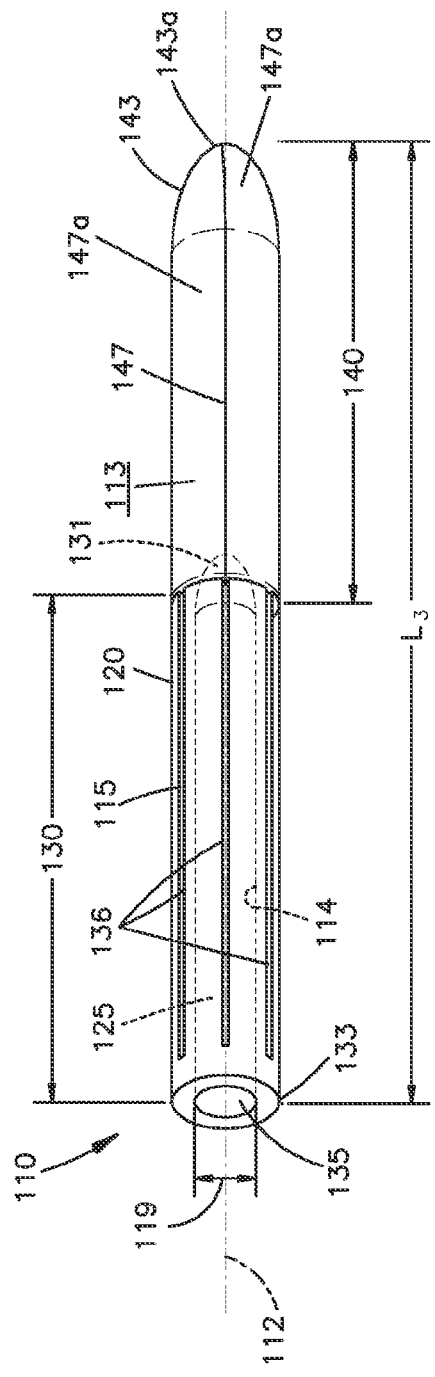
FIGS. 3A-D illustrate side perspective and top plan views, respectively, of a bone augmentation device and its method of use in accordance with a preferred embodiment of the present invention.
Figure 3B:
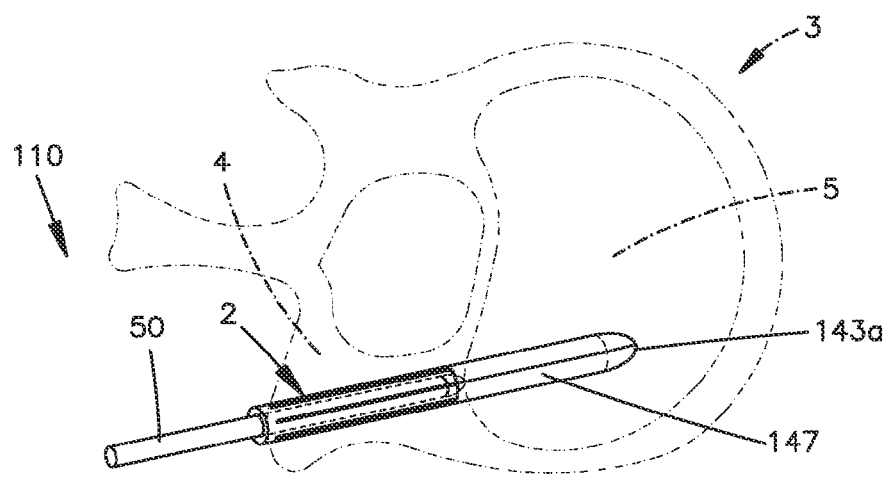
Figure 3C:
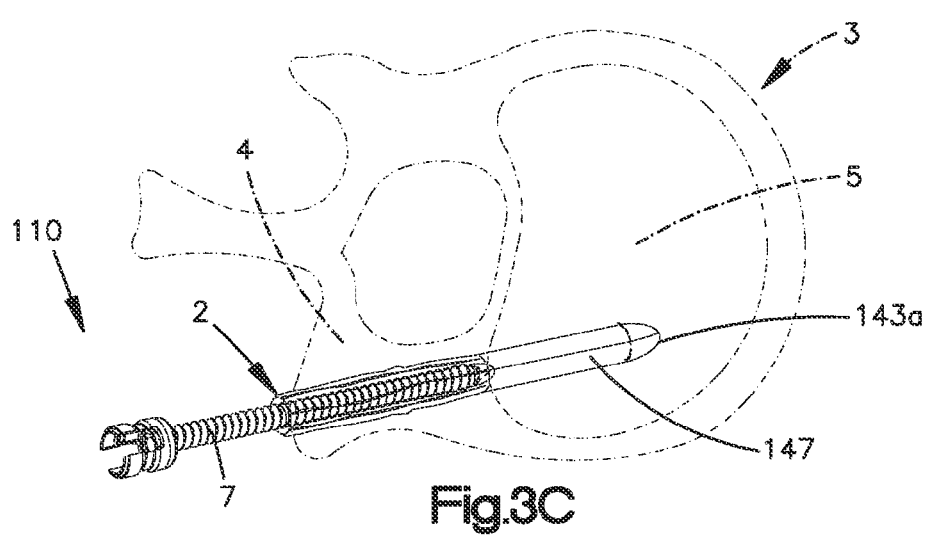

In operation, and in reference to FIG. 3B, the implant 110 is preferably inserted into a preformed hole 2 extending into what may be an osteoporotic vertebral body 5 through a pedicle 4 using an instrument 50 such as a trocar or plunger rod. A suitable insertion instrument used in association with the bone augmentation devices is discussed in detail in reference to FIG. 8. The implant 110 preferably is inserted into the bone preferably so that the proximal end 133 is relatively flush and even with the opening 2 in the bone. A pedicle screw 7 is then preferably inserted into the vertebra 3 through the implant 110 as shown in FIG. 3C. As the pedicle screw 7 progresses through the sleeve 120, the slits 136 disposed along the proximal portion 130 of the allograft sleeve 120 spread apart and preferably enable substantially the entire proximal portion 130 to expand radially within the channel in the pedicle 4, as shown in FIG. 3C, to provide bite into the pedicle 4 through which the proximal portion 130 is disposed. In a preferred embodiment, the screw threads of the pedicle screw 7 preferably deform the softer proximal portion 130 such that threading is formed in the hollow interior wall surface 114 of the proximal portion 130.

Figure 3D:
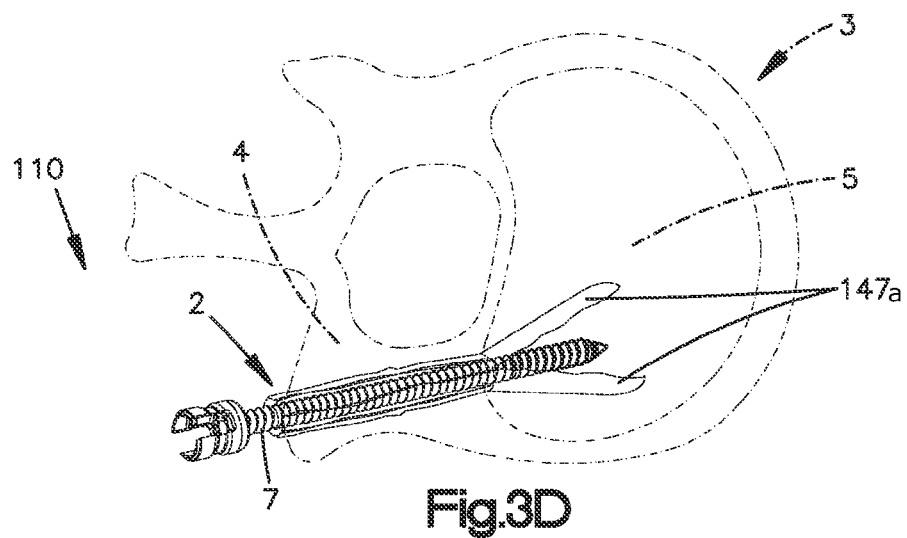

As the pedicle screw 7 progresses through the implant and contacts the interior of the distal portion 140, the distal portion 140 splits apart via the slits 147 formed there through as shown in FIG. 3D and presses into the trabecular bone that may be present and forms a wedge between the screw 7 and the posterior wall of the pedicle 4, providing additional pull out resistance to the pedicle screw 7. The distally expanded distal portion 140 of the allograft sleeve 120 and the radially expanded proximal portion 130 of the sleeve 120 preferably improves the purchase of the pedicle screw 7 into the surrounding bone and preferably reduces the likelihood of pedicle screw backout and toggling.

A biocompatible material, such as PMMA, calcium phosphate cement, etc. may be used in conjunction with the allograft implant 110 and pedicle screw 7 placement, such as through the distal end of the pedicle screw, along the distal portion of the implant and/or pedicle screw, or along the entire interior of the implant while still in a liquid state.

FIGS. 4A-C show a further preferred embodiment of bone augmentation device 210 in the form of an allograft tube or sleeve 220 that is preferably completely demineralized (e.g., at least 80% demineralized). While it is preferred that the sleeve 220 be completely demineralized, the sleeve may be partially demineralized, have no demineralization, or have inner and outer surfaces completely or partially demineralized to a different extent than the mid portion of the sleeve 220. The allograft tube 220 preferably includes a longitudinal axis 212 and has a central bore 225 so that the sleeve 220 is hollow throughout its entire length having a proximal and a distal opening 235, 245. The allograft tube or sleeve 220 may further include a tab (not shown) on its proximal end 233 to serve a similar purpose to the tab 23 of the second preferred embodiment.

In operation, the preferably, completely demineralized allograft sleeve 220 is preferably inserted into a previously formed hole through a pedicle 4 and into the interior of a vertebral body 5. The allograft sleeve 220 is preferably inserted such that the proximal end 233 of the allograft sleeve lies flush with an exterior surface of the pedicle 4 as illustrated for the sleeve 120 in the embodiment of FIGS. 3B-D. A pedicle screw 7 is preferably inserted though the allograft sleeve 220 and surrounding pedicle and vertebral bone, and as the pedicle screw progresses toward the interior of the vertebral body 5, the demineralized bone material of the allograft implant 210 is pressed into the pedicle 4 and the interior of the vertebral body 5, which may be characterized by cancellous bone.

The demineralized nature of the allograft implant preferably enhances the osteo-inductive potential of the allograft implant, and the interference fit between the screw, allograft implant and the wall of the pedicle 4 that results from the progression of the pedicle screw 7 through the allograft sleeve 220 increases the pull-out strength of the pedicle screw. Alternatively, the allograft sleeve 20 may be only partially demineralized on the external and/or internal surface of the allograft sleeve 220. The external surface 213 of the proximal and/or distal portion of the allograft sleeve 220 may include surface texturing to improve purchase between the allograft sleeve 220 and the surrounding bone 3.

The allograft sleeve 220 may include a distal portion 240 that is partially demineralized and a proximal portion 230 that is completely demineralized. In operation, a pedicle screw 7 preferably advances easily in the pedicle 4 owing to the presence of the completely demineralized softer allograft bone in the proximal portion 230 of the allograft sleeve 220 yet provides enough bite to secure its position therein. As the pedicle screw 7 advances beyond a posterior wall of the vertebral body 5, and into the distal portion 240 of the allograft tube 220, the stronger, thicker bone of the allograft sleeve 220 is expanded and/or spread into what may be the cancellous core of the vertebral body. The external surface 213 of the proximal and/or distal portion of the allograft sleeve 220 may include surface texturing to improve purchase between the allograft sleeve 220 and the surrounding bone. The distal end 243 of the allograft sleeve can be cross-pinned, e.g., with an allograft pin (not shown), to assist in facilitating the insertion of the allograft sleeve. Cross pinning would also improve the visibility of the implant on C-arm.

The allograft tube or sleeve 220 may alternatively include a longitudinal axis 212 and central bore 225 that extends from the proximal opening 235 to the distal opening so the sleeve 220 is hollow throughout its entire length. The tube 220 may include one or more longitudinal slits, slots, grooves or perforations 247 extending in the direction of the longitudinal axis 212 in the mid-section of the tube 220. Preferably, the slits 247 extend through the tube wall 215 from the exterior surface 213 to the internal wall surface 214. The slits 247 preferably do not extend the entire length of the sleeve 220 and preferably do not extend to the distal end 243 or the proximal end 233. Preferably a continuous ring section 239 is formed at the proximal end 233, and a continuous ring section 251 is formed at the distal end 243. The continuous ring sections 239, 251 preferably are about two millimeters (2 mm) to about ten millimeters (10 mm) in length, more preferably about three millimeters (3 mm) to about seven millimeters (7 mm). The wall surface 215 at the ring sections 239, 251 preferably is continuous and uninterrupted by the slits 247. The ring sections 239, 251 preferably remain intact upon insertion of the screw. The mid-section of the tube 220 containing the slits, or at least a portion thereof, is preferably thicker than the continuous ring sections 239, 251.

The outside diameter 217 of the tube 220 is preferably selected to fit within the hole prepared in the bone, while the inside diameter 219 of the tube 220 accepts the screw 7. The inside diameter 219 of the ring sections 239, 251 are preferably larger than the mid-section and preferably should be roughly the same size as the outside diameter of the screw 7 so that the screw 7 can be inserted with relatively little expansion of the ring sections 239, 251 so that the ring sections 239, 251 preferably remain intact. The inside diameter 219 of the mid-section of the sleeve 220 preferably interferes with the screw as the screw is inserted down the sleeve 220 to expand the mid-section as shown in FIG. 4C. That is, as the screw 7 progresses down the mid-section, the screw 7 expands and spreads the slits 247 as shown in FIG. 4C. The expansion of the mid-section improves the holding strength and purchase of the screw 7 in the bone and preferably resists or prevents toggling of the screw 7 which may cause the screw 7 to shift in the vertebra 3.

While the embodiments of FIGS. 4A-C have been shown and described as employing slits 247 that extend through the entire wall thickness from the interior surface 214 to the exterior surface 213, slits that extend only partially through wall 215 may be used, and the slits 247 may comprise open slots, grooves or perforations. In addition, while the tube or sleeve 220 has been described as being formed of allograft, and preferably at least partially demineralized allograft, sleeve 220 can be formed of any biocompatible material including metals, metal alloys, ceramics, composites, and plastics, such as, for example, PEEK, PTU, PET, EVA, PCU or other biocompatible or bioresorbable plastics, and the other embodiments of the present application may also be constructed of these different materials.

FIGS. 5A-C show a modification to the designs of the allograft sleeve described in the embodiment of FIG. 4 wherein the distal portion 240 is etched or grooved to weaken the allograft of the distal portion 240 along a parting line 249, or completely cut into strips, such that the distal portion 240 splits open when the pedicle screw 7 advances through the distal interior of the allograft tube 220 and, thereby, further resists, or prevents pullout. The embodiments of FIGS. 4 and 5 may be formed monolithically from the same single piece of allograft tissue, or in the alternative may be formed from separate allograft pieces and thereafter coupled together.

FIGS. 5D-E show a further embodiment to the designs of FIG. 4 and FIGS. 5A-C. The bone augmentation device 210' has a proximal continuous ring section 239 having a wall 215 that defines an opening 235 at the proximal end 233. The opening 233 communicates with a hollow cavity 225. Preferably a plurality of strips 253 extend distally from the wall of the ring section 239. The bone augmentation device 210' is preferably monolithic and may be formed from a hollow cylindrical shaped monolithic tube or sleeve that has a continuous cylindrical wall that has a plurality of, in this example, eight, slits 249 cut into the sleeve, all in the distal portion to form thin strips 253. The slits 249 may extend into the proximal portion 230 of the sleeve 220 as shown. The slits 249 preferably extend from the interior wall surface 213 to the exterior wall surface to form uncoupled strips. In the alternative or additionally, the slits 249 may only extend partially through the wall 215 and may tear and detach as the screw progresses down the sleeve 220.

FIGS. 6A-C show another embodiment of a bone augmentation device 310, and a method of making the same. The bone augmentation device 310 preferably is formed from two pieces 360, 370 and in its assembled form is generally a cylindrically shaped elongated member 320. The elongated member 320 preferably includes a relatively thicker and stiffer distal portion or component 340 and a relatively thinner proximal portion or component 330. The distal component 340 includes a ring-like proximal end 362, one or more fingers 364 separated by gaps or space 363 and a connector portion 365. The connector portion 365 preferably flexibly connects the fingers 364 to the ring-like proximal end 362.

The proximal component 330 includes a ring-like connector strip 372, and one or more extremities 374, separated by gaps or space 373. The connector strip 372 connects the extremities 374 extending from the connector strip 372. Both the proximal component 330 and distal component 340 are preferably formed from allograft bone, although other materials are contemplated. Preferably both the proximal and distal components 330, 340 are formed of completely or partially demineralized bone, although it may be preferred that the proximal component 330 be completely demineralized while the distal component 340 is only partially demineralized bone, and the distal portion 310 preferably is relatively stiffer than the proximal component 330. The proximal component 330 and the distal component 340 are each preferably formed from a single piece of bone and are connected together as discussed below.

Preferably the thickness 318 of the walls 315 of the proximal component 330 is less than the thickness 318 of the walls 315 of the distal component 340. The inner diameter 319 of the elongated member 320 is preferably slightly smaller than or equal to the outer diameter of the pedicle screw 7 inserted down the hollow channel 325 formed in the sleeve 320. Preferably a groove 361 separates the fingers 370 from the ring 362 to form the flexible connector portion 365. The width of the groove 361 is sufficient in size to fit the width of the connector strip 372 when the components 330, 340 are joined together as illustrated in FIG. 6C. A groove or recessed portion 366 is formed in the ring section 360 to accommodate the extremities 374 when the proximal component 330 is assembled to the distal component 340.

To assemble this preferred elongated member 320, the fingers 364 of the distal component 340 may be pinched together as illustrated in FIG. 6B. When fingers 364 are pinched together, the connector portion 365 acts as a flexible hinge permitting the fingers 364 to move closer together. With the fingers 364 pinched, the proximal component 330 is inserted and slides over the distal component 340. The fingers 364 preferably are inserted down gaps 373 while the extremities 374 correspond to and are slid down the space 363. The distal component 340 and the proximal component 330 are urged together so that the fingers 364 extend past the connector strip 372 and the extremities 374 extend past the rigid ring section 362 as shown in FIG. 6C. Preferably, the extremities 374 extend and slide through the recesses 366 formed in the ring section 362. Preferably the connector strip 372 of the proximal component 330 fits within the groove 361 formed in the connector section 365, and preferably is secured into the distal component 340. After the two pieces 360, 370 of allograft bones are assembled together to form the implant 310 the implant 310 may be immersed in an acid bath to secure or weld the pieces 360, 370 together.

Alternatively, the proximal portion 330 may be moved relative to and connected to the distal portion 340 without pinching the fingers 364, if the fingers 364 fit within the gaps 373 and the extremities 374 fit with the gaps 363. In this assembly method, the connector portion 365 preferably will be sufficiently flexible to permit the connector strip 372 to slide over the arms 364 and fit within the groove 361.

While the embodiment of FIGS. 6A-C has been described and illustrated with two fingers 364 separated by two gaps 363, and the two extremities 374 separated by two gaps 373, the implant 310 may include more or less fingers 364 and extremities 374, and there may be an unequal number of fingers and extremities 364, 374. The potential advantage of the two-piece bone augmentation device 310 is that it can be formed from two shorter pieces of allograft or autograft bone that may be easier to harvest than an appropriate sized single piece of bone.

Referring to FIGS. 7A-C, a bone augmentation device 410 in accordance with another preferred embodiment in the form of sleeve or tube 420 preferably is formed of allograft tissue and preferably includes a longitudinal axis 412 and proximal and distal ends 433, 443. The sleeve 420 preferably also includes a plurality of longitudinal cuts 447 formed in such a way that the proximal end 433 and the distal end 443 of the sleeve 420 remain as continuous rings while the middle portion is formed into thin strips 453. The sleeve 420 is preferably partially or completely demineralized subsequent to the formation of the longitudinal cuts 447. The distal portion of the strips 453 are preferably formed in such a way that the strips 453 have thin sections 438 at or near their halfway point that preferably serve as flexible hinges 438a that preferably form a fold line. The thinner sections 438 of the strips 453 are preferably located at approximately three quarters (¾) of the length of the hollow tube 420 from the proximal end 433.

In operation, a pushrod 50 is preferably used to insert the hollow sleeve 420 into a pedicle 4 until the proximal end 433 lines up with the outside of the pedicle 4 and a halfway mark on the sleeve 420 lines up against or near the interior of the posterior wall of the vertebral body 5 as shown in FIG. 7B. The distal end 443 of the sleeve 420 is then preferably pulled back while retaining the proximal end 433 at its position flush with the exterior of the pedicle 4. As the distal end ring section 433 is pulled proximally, the distal portion 440 folds in half at the hinges 438 as shown in FIG. 7C and, after a certain amount of retraction, locks up into its folded position. The pullout strength of the sleeve 420 may be thereby improved.

The distal continuous ring 443 may be pulled back toward the proximal portion 430 in a number of different ways. The end of the pusher 50 may attach to the distal continuous ring 443 and the pusher 50 can be retracted to move the ring 443 proximally. The pusher 50 can be disengaged from the continuous ring 443 when the ring 443 has been moved proximally so that the hinges 438 have been activated and the distal portion 440 folded and expanded. The distal continuous ring 443 of the sleeve 420 may alternatively include internal threads (not shown). The internal threads may interact with threading on the distal end of the pusher 50 to connect the pusher 50 to the distal continuous ring 443. The pusher 50 is then pulled proximally to retract the distal end 443 toward the proximal end 433 of the sleeve 420. As the distal end 443 is retracted or pulled back toward the proximal end 433, the distal portion 440 folds at the hinges 438 and expands in the distal portion 440 to provide better purchase in the vertebra 3. The pusher 50 can then be disconnected from the sleeve 420. Alternatively, a threaded rod may be used to deploy the expandable distal portion 440 by interacting with the threads on the continuous ring 443. The threaded rod can be rotated to move the ring 443 proximally along the length of the threaded rod. Alternatively or additionally, the threading on the distal continuous ring 443 may interact with the threads on the pedicle screw inserted into the sleeve 420 to retract and move the distal portion 440 to its expanded position as the pedicle screw is rotated into position. Additionally, or alternatively, a separate nut (not shown) may be provided at the distal end of the sleeve 420 to work in conjunction with a threaded rod or pedicle screw 7 to deploy the expandable distal portion 440.

FIG. 8 shows an insertion instrument that is suitable for use with the implants, and particularly the implant embodiments of FIGS. 1-7. The insertion instrument serves to implement a simple push or plunge function to the bone augmentation device 10, 10', 110, 210, 210', 310, 410, via the pusher element 50. The pusher element 50 preferably includes a stop 52 that comes to rest on the posterior wall of the pedicle 4 that serves to limit the length of the implant 10 inserted into the pedicle 4 and vertebral body 5. The insertion instrument is preferably radiolucent so as to enable the correct positioning of the implant, allograft sleeve, tube, elongated member or shim 10, 10', 110, 210, 210', 310, 410.

While the implants of FIGS. 1-7 have been generally shown and described as cylindrical, it can be readily appreciated that the outer shape, and inner bore shape can take other forms and is not limited to the cylindrical shape shown and described. The allograft tissue forms of the present invention may be used in a freeze-dried state during implantation and then allowed to rehydrate in situ, or during the implant procedure. Backward teeth, ridges, reverse buttresses, threads, one or more keels or other surface texture can be applied to the exterior surface of the implants 10, 10', 110, 210, 210' 310, 410 to increase bite into the surrounding bone. Completely or partially demineralized allograft bone sticks (not shown), similar in shape and size to toothpicks, or match sticks, can be used as shims between pedicle screws 7 and the surrounding bone into which the pedicle screws 7 are inserted.

The orientation, location, depth and length of the slits, slots, grooves, cuts or perforations in the plugs or shims can be configured such that the amount of and location of expansion can be controlled, for example, expansion of the distal portion can occur in a preferred plane. Radiographic markers (not shown) can be added to the implants, to help identify the orientation of the implants or portions thereof within the pedicle 4 and/or vertebral body 5. The implants are not limited to allograft bone construction and may include material compositions other than or in addition to allograft bone, such as any other suitable biocompatible material now or hereafter known including, but not limited to, plastics (e.g., PEEK, PTU, PET, EVA, PCU or other biocompatible or bioresorbable plastics), thermoplastics, rubber, titanium, stainless steel, titanium alloy, metal alloys, ceramic, etc.

Figure 9A:
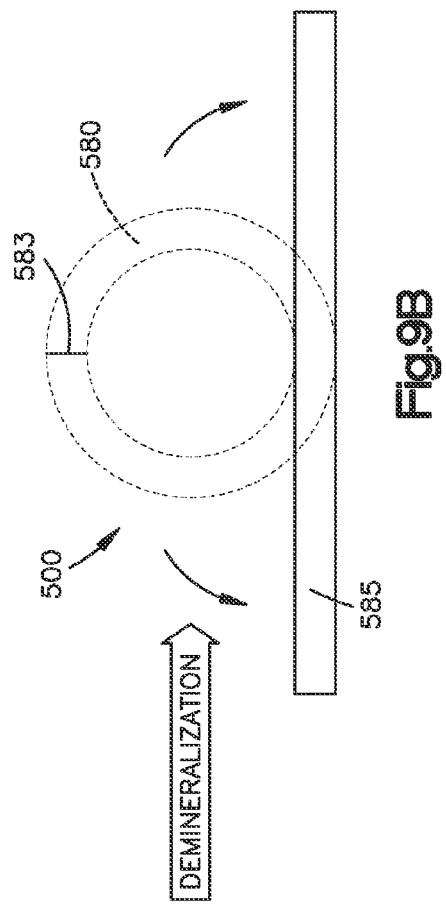
FIGS. 9A-C illustrate steps taken during a first preferred method for forming a bone augmentation device in accordance with the present invention.
Figure 9B:
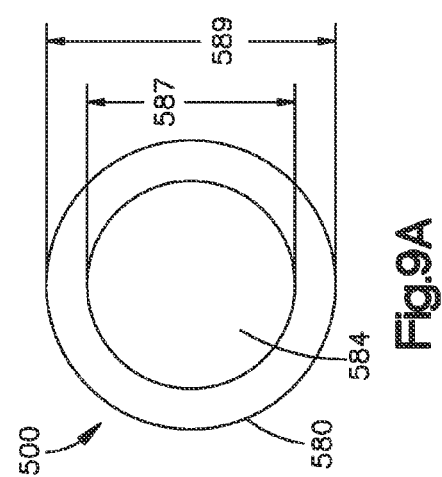
Figure 9C:
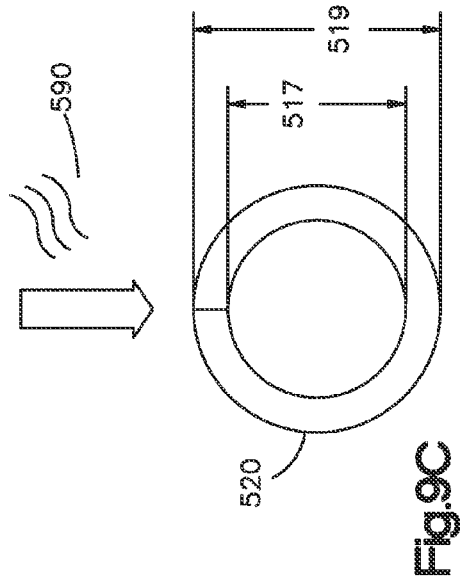

Referring to FIGS. 9A-C, a method of forming an allograft tube 520 in accordance with one preferred embodiment that includes having smaller outer and inner diameters 517, 519 than the outer and inner diameters 587, 589 of the original donor bone, and an implant 510 resulting from the method is shown. FIG. 9A includes a donor bone 580, such as a tibia or femur, having an outer diameter 587 and an intramedullary canal 584 defining an inner diameter 589. A cut 583 is made in the donor bone 580, the donor bone 580 is demineralized and thereafter unrolled resulting in a sheet 585 as shown in FIG. 9B. The sheet 585 may be trimmed to a desired length and width. Thereafter, the sheet 585 may be rolled up to form a tube or sleeve 520 as shown in FIG. 9C having an outer diameter 517 and an inner diameter 519. Electromagnetic radiation 590 may be applied to the demineralized bone to form a weld between the two ends of the sheet 585 in order to weld the ends of the sheet 585 together to form hollow tube 520. The allograft tube 520 is at least partially demineralized and is configured to provide enhanced purchase between a pedicle screw and a hole into the interior of a vertebral body 5, as well as enhance osteointegration of the tube 520 within the vertebra 3. The two ends of the sheet 585 may also be compressed together and subjected to demineralization bath to secure or weld the ends together.

The donor bone 580 preferably is completely demineralized such that the sheet 585 can be produced by forming the cut 583 and unrolling the donor bone 580 to form the sheet or planar structure 585. The sheet 585 is then trimmed to a desired length and width from which the desired characteristics, including circumference, inner diameter 519, and outer diameter 517, and length L, of the allograft tube 520 is be provided. Slits, slots, grooves, perforations, and differences in wall thickness can also be formed and manufactured in the sheet 585. The sheet 585 is then rolled back into a tubular form and electromagnetic radiation 590, e.g., from an Nd—YAG laser (Neodymium-doped Yttrium Aluminum Garnet) is applied to the area 591 where the ends abut to form a weld, resulting in the allograft tube 520.

The allograft tube 520 can be inserted into a hole through a pedicle 4 and into the interior of a vertebral body 5, such that the proximal end 530 of the allograft tube 520 lies flush with the exterior surface of the pedicle 4. A pedicle screw 7 is inserted though the allograft tube 50 and surrounding pedicle 4 and vertebral bone and, as the pedicle screw 7 progresses toward the interior of the vertebral body 5, the demineralized bone material of the allograft tube 520 is pressed into the pedicle 4 and the interior of the vertebral body 5, which may be characterized by cancellous bone. The demineralized nature of the allograft tube 520 enhances the osteo-inductive potential of the allograft tube 520 and the pressed material that results from the progression of the pedicle screw through the allograft tube 520 increases the pull-out strength of the pedicle screw 7.

FIG. 10A-E illustrate an alternate method of forming an allograft tube 620 that is similar to the allograft tube 520. All elements described in reference to FIG. 10A-E are similar to those described in FIG. 9A-C, with the exception of a female dovetail 637, a male dovetail 657, and a joint 659 formed from the female and male dovetails 637, 657.

In operation, and in continuing reference to FIGS. 10A-E, the allograft tube 620 is formed from a donor bone 682 wherein the outer and inner diameters 617, 619 of the allograft tube 620 are smaller than the outer and inner diameters 687, 689 of the donor bone 682. Similar to the first steps of the method 500, the donor bone 682 is demineralized, cut, and unrolled into a flat sheet 685. The sheet 685 is trimmed to the desired dimensions and one or more female and male dovetails 637, 657 are cut into the edges of the sheet 685. The sheet 685 is then rolled into a cylindrical form and the female and male dovetails 637, 657 are mated together to form the joints 659, and thereby secure the allograft tube 620 together. Additionally, biocompatible adhesive and/or electromagnetic radiation can be used to further enhance the strength of joint

659. Further the joints 659 may be subjected to a demineralization acid or fluid to secure or weld the joints 659 together.

FIGS. 11A-B illustrate a method 700 for forming an allograft tube 720 in accordance with a further preferred embodiment that has smaller outer and inner diameters 717, 719 than the original donor bone 782. The allograft tube 720 forms a bone plug implant 710. Tabs 722 and 724 are preferably formed on alternate sides of a slot 726 formed through the donor bone 782. A slab 727 having a plurality of holes 728 and generally formed as a rectangular piece of demineralized allograft bone is configured to be received into the slot 726. A plurality of dowel pins 775 are configured to be received through the matching holes 728, 721 as shown in FIG. 11B.

In operation, and in continuing reference to FIGS. 11A-B, an allograft tube 720 is formed from a donor bone 782 wherein the outer and inner diameters 717, 719 of the allograft tube are smaller than the outer and inner diameters 787, 789 of the donor bone 782. The donor bone 782 is cut along its length to form the slot 726 and tabs 722, 724. The holes 721 are drilled into the tabs 722, 724. The donor bone 782 is then demineralized. The tabs 722, 724 and, optionally, the holes 721 are masked during the demineralization process to retain their rigidity. Another piece of demineralized allograft bone is then cut into a rectangular form to produce the slab 727 and a plurality of holes 728 are drilled through the slab 727. The slab 727 and the holes 728 are configured to mate with the tabs 722, 724 and the holes 721 formed on the donor bone 782. Appropriate sized dowel pins 775 are cut from bone and the allograft tube 720 is assembled together by mating the slab 727 to the tabs 722, 724 and aligning the plurality of holes 721 with the plurality of holes 728. The plurality of pins 775 are then inserted through the plurality of holes 721, 728. Once the allograft tube 720 is assembled, the allograft tube 720 can be demineralized again to fuse the connections formed between the slot 726 and the slab 727, as well as between the pins 775 and the holes 721, 728.

Figure 12A:
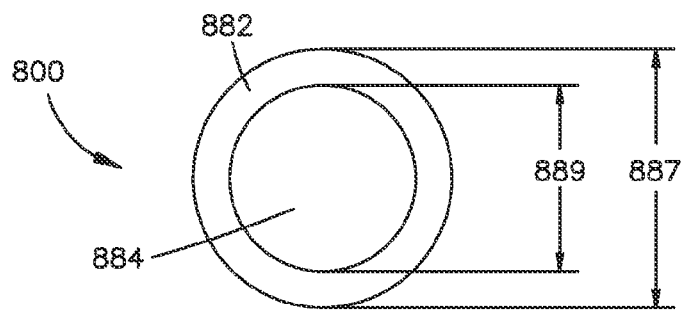
FIGS. 12A-F illustrate steps taken during a fourth preferred method for forming a bone augmentation device in accordance with the present invention.
Figure 12B:
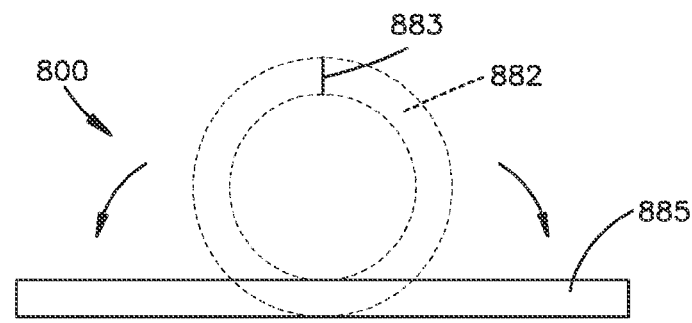
Figure 12C:
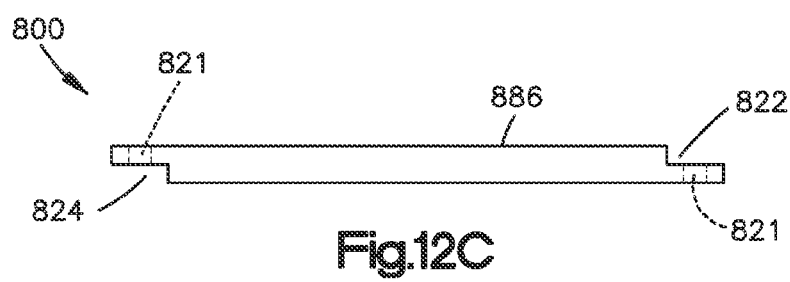
Figure 12D:
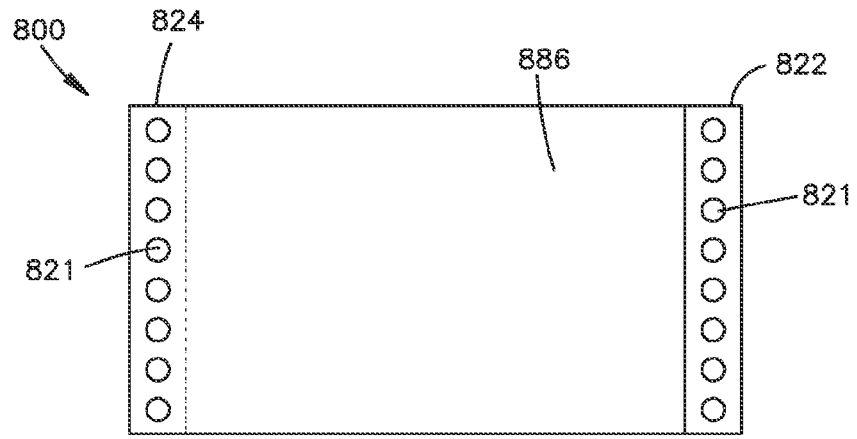
Figure 12F:
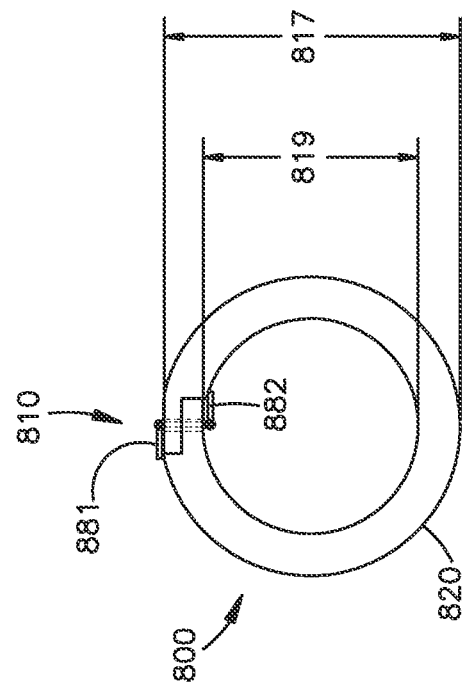
Figure 12E:
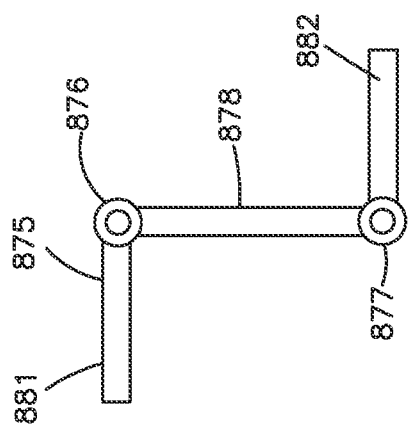

FIGS. 12A-F illustrate a method 800 for forming an allograft tube 820 in accordance with another preferred embodiment that has smaller outer and inner diameters 817, 819 than the original donor bone 882. The tube 820 results in an implant 810 for preferably increasing the holding strength and purchase of a bone screw. Mating tabs 822, 824 preferably are formed on alternate sides of the sheet 885 which was formed by cutting, unrolling and trimming the donor bone 882. A plurality of holes 821 are formed through the tabs 822, 824 as shown in FIGS. 12C-D. A plurality of dowel pins 875 are configured to be received through the holes 821. The pins 875 include a plurality of right angles, such as a capital "I" shape or "Z" shape, with the corners of the "Z" shape preferably formed at right angles as opposed to oblique angles. The pins 875 are formed from bone and the right angle portions included therein are demineralized to the point of flexibility such that a plurality of hinges 876, 877 are formed at the right angle portions such that the pins 875 can be flexed at their hinges 876, 877 into a straight configuration during insertion through the straight holes 821 and spring back into their original "I" or "Z" shape subsequent to being inserted through the holes 821.

In operation, and in continuing reference to FIGS. 12A-E, the allograft tube 820 is formed from a donor bone 882 wherein the outer and inner diameters 817, 819 of the allograft tube 820 are smaller than the outer and inner diameters 887, 889 of the donor bone 882. The donor bone 882 is demineralized, cut, and unrolled into a flat sheet 885. The sheet 885 is trimmed to the desired dimensions, mating tabs 822, 824 are cut, and the holes 821 are drilled through the tabs 822, 824 to form the sheet 886. The sheet 886 is then rolled into a cylindrical form and the tabs 822, 824 are overlapped such that the holes 821 through both of the tabs 822, 824 are aligned. As the pins 875 are inserted through the overlapping holes 821, the flexible hinges 876 and 877 straighten out temporarily and spring back to their initial configuration upon being positioned appropriately with respect to the holes 821, i.e., the longer shaft portion 878 of the pins 756 are inside and traverse the holes 821 and the top and bottom transverse portions 881, 882 protrude and lie transversely atop holes 821. Additionally, biocompatible adhesive and/or electromagnetic radiation and/or additional demineralization can be applied to further enhance the securement of the pins 875 within the holes 821. Upon assembly, the allograft tube 820 has smaller outer and inner diameters 817, 819 than the outer and inner diameters 887, 889 which characterize the original donor bone 882.

FIGS. 13A-B illustrate an allograft tube 920 in accordance with another preferred embodiment that may be identical or similar to any of the allograft tubes 520, 620, 720, or 820 described above or, alternately, may result from a donor bone 982 that is demineralized, sliced open, flattened into a sheet, cut to the desired dimensions, and re-rolled into a tubular form that does not include any mechanical securement mechanisms, such as the weld resulting from the application of radiation 590, the dovetail joint 659, the slab 727 and pins 775, or the holes 821 and pins 875.

Alternatively the donor bone 982 may be formed into a relatively flat sheet of a desired length, for example forty millimeters (40 mm), and a desired thickness, for example, about half a millimeter (0.5 mm) to about two millimeters (2 mm), preferably about seventy five hundredths of a millimeter (0.75 mm). The sheet may be supplied to the surgeon as a sheet and may be demineralized and/or freeze dried and the surgeon can cut the sheet to a desired width, during the surgery or just prior to surgery, depending upon the diameter of the hole and the diameter of the implant. The surgeon can roll the sheet into tubular form and insert it into the hole. The screw may thereafter be inserted into the hole in the bone with the sheet material in rolled or strip form preferably increasing the purchase and holding strength of the screw.

The preferred method further includes a tube 955 that can be formed from metal or plastic and into which allograft tube 920 is inserted. In operation, and in reference to FIG. 13A, the allograft tube 920 may be formed as described above and inserted into the tube 955. The allograft tube 920 may be freeze dried while inside the tube 955, or may be freeze dried and then inserted in the tube 955. The freeze-dried allograft tube 920 preferably remains inside the tube 955 during packaging and shipping. Alternatively, the implant 920 may be inserted in the tube 955 prior to or during surgery. The tube 955 is then aligned with a preformed pilot hole in a pedicle 4 of the vertebral body 5 and the plunger 950 or a push rod is advanced with respect to the tube 955 to push the allograft tube 920 into the pedicle to serve as an augmentation or guard device or, in an alternate embodiment, into the interior of the vertebral body 5 to serve as a vertebral body augmentation filler. Upon the introduction of the allograft tube 920 into the pedicle 4, the allograft tube 920 undergoes in situ rehydration upon coming into contact with blood and other biomaterial, thereby expanding to fit securely within the hole formed through the pedicle. Alternatively, the tube 955 may be inserted into the hole, which is to receive the screw. A push rod 950 is placed in the tube and may abut the proximal end of the implant. The tube 955 is thereafter withdrawn over the push rod 950 so that the implant 920 remains in position in the hole. The implant may then rehydrate upon coming into contact with blood and other biomaterial. This alternative method may better protect the implant during the insertion procedure, particularly protect the more fragile, flexible or floppy implants so that they are properly positioned and remain intact.

FIGS. 14A-B illustrate an allograft tube 1020 in accordance with another preferred embodiment that is formed in a manner similar to the allograft tube 920, except that it is rolled helically to form a spiral tubular structure, as opposed to the cylindrical allograft tubes 920. The allograft tube 1020, upon freeze drying, preferably is characterized by an outer diameter that is smaller than its outer diameter upon rehydration and smaller than the diameter of the pedicle hole into which it is intended to be implanted. As such, the allograft tube 1020 is configured to fit a variety of hole sizes formed into a pedicle 4 and the yield of the implant formed from the available donor tissue 1082 is enhanced. The use of freeze dried allograft tube 1020 further avoids interference experienced during its insertion into a pedicle hole by avoiding contact with any irregularities in the wall of the pedicle due to its reduced pre-rehydration diameter.

In operation, and in continuing reference to FIGS. 14A-B, the allograft tube is helically wound and freeze-dried. The allograft tube 1020 is then manually inserted into a hole formed in a pedicle 4 and, upon contact with blood and other biomaterial inherent to the interior of the pedicle 4, rehydrates and expands, preferably fitting snugly within the hole to provide a pedicle augmentation device or guard, as described above, for subsequent pedicle screw 7 insertion. The helically wound implant 1020 may be inserted using the method and instruments described above for FIG. 13, or using the inserter instrument described in FIG. 8.

Referring to FIG. 15, a preferred inserter 1091 useful for the insertion of the allograft tube 1020 is provided. The inserter 1091 may also be used to insert the implants of FIGS. 1-12. Inserter 1091 includes an inner shaft 1092 having a spreading cone 1093 at its distal end 1094. The inner shaft 1092 is coupled to a cannulated outer sleeve 1095 via one or more pins 1096 extending transversely from the inner shaft 1092 and through the outer sleeve 1095. The one or more pins 1096 may be welded to, screwed to, or otherwise securely coupled to the inner shaft 1092 and outer sleeve 1095. The outer sleeve 1095 further includes an opening 1097 at its distal end 972. The inserter 1091 further includes a plunger 1099 that includes a hollow distal portion 1100 configured to mate with the inner shaft 1092. The plunger 1099 moves axially, along the longitudinal axis of the inserter 1091, relative to the inner shaft 1092 and the outer sleeve 1095. The plunger 1099 includes one or more slots 1068 configured to slidingly receive there through the one or more pins 1096. The number of slots 1068 disposed through the plunger 1099 preferably corresponds to the number of pins 1096 included in the inserter 1091. The one or more pins 1096 are configured to prevent overextension of the plunger 1099 with respect to the inner shaft 1092 and, as a result, prevent over insertion of the allograft tube 920 into the pedicle hole, as well as to maintain the distal end of the spreader cone 1093 aligned with the distal end 1098 of the outer sleeve 1095.

In operation, and in continuing reference to FIGS. 14A-15B, the helically wound, freeze dried allograft tube 920, 1020 is loaded into and stored within the inserter 1091 concentrically around the inner shaft 1092. Any of the other implants described herein as well as other implants, alternatively and additionally may be loaded into and inserted using inserter 1091. Prior to surgery, the allograft tube 920, 1020 may be rehydrated while inside the inserter 1091 using a rehydrating agent such as saline. The distal end of the inserter 1091 is placed adjacent to the vertebral body 5 (as shown in FIG. 15A) such that the opening 1097 in the distal end 1098 of the outer sleeve 1095 is aligned with the hole 2 formed through the pedicle 4. The plunger 1099 is advanced with respect to the outer sleeve 1095 and the inner shaft 1092, and guided via the interaction of the one or more pins 1096 with the corresponding one or more slots 1068. As the plunger 1099 advances, the distal end of the plunger 1099 engages the proximal end 933 of the allograft tube 920 and causes the allograft tube 920 to advance within and out the distal end of the inserter 1091. As the allograft tube 920 advances distally along the inner shaft 1092, the allograft tube 920 advances over the spreader cone 1093, causing the allograft tube 920 to radially expand (e.g., unwind), just prior to implantation into the hole formed in the pedicle 4. Depending upon the implant used the spreader cone 1093 may or may not expand the implant. The one or more pins 1096 engage the terminal ends of the one or more slots 1068 upon optimal advancement of the allograft tube 920 with respect to the pedicle hole to prevent over insertion of the allograft tube 920.

Alternatively the inserter 1091 may be utilized in a different method. In the alternative method the implant is loaded within the inserter and around the inner shaft 1092 and the distal end of the inserter 1091 is inserted into the hole prepared in the bone where the bone augmentation device is to be inserted. The plunger 1099 is advanced with respect to the outer sleeve 1095 so that it engages the proximal end of the implant. The plunger 1099 is moved with respect to the outer sleeve 1095 to retract the outer sleeve 1095 and spreader cone 1093 out of the bone while the implant remains within the bone and in the hole as the inserter 1091 is withdrawn from the bone. As the outer sleeve 1095 and spreader cone 1093 are withdrawn from the bone, the implant will pass over the spreader cone 1093, which preferably expands, unfurls, and/or uncoils the implant to a larger size. Accordingly, a relatively small diameter instrument 1091 with a compacted bone augmentation device may be inserted into a relatively small hole to receive a bone screw, the inserter 1091 is operated to pull back the outer sleeve 1095 and the bone augmentation device is expanded and deployed in the bone in a larger size than its inserted size.

Referring to FIG. 16, a preferred embodiment of a screw augmentation system that includes an allograft tissue form and a bone screw is shown. A pedicle screw 7 that is inserted into a vertebral body 5 through a pedicle 4 preferably includes one or more radial holes 8 through the minor axis of the pedicle screw's shaft that can be radiographically visualized intraoperatively. These radial holes 8, when positioned at an appropriate orientation, may serve as guides to drill a cross hole through the pedicle 4 subsequent to insertion of the pedicle screw such that the cross holes formed in the pedicle 4 and the radial holes 8 of the pedicle screw 7 line up.

A strip of allograft bone 29 is preferably used in conjunction with the radial holes 8 of the pedicle screw 7 that preferably includes two demineralized opposite end portions that are flexible and a short, stronger, partially demineralized middle portion. The allograft strip 29 is preferably inserted through the cross holes of the pedicle 4 and the radial holes 8 of the pedicle screw such that the stronger middle portion of the allograft strip 29 sits as a pin within the radial holes 8 of the pedicle screw. A knot can be tied around the posterior elements of the vertebra using the flexible opposite end portions of the allograft strip 29 and thus securing the pedicle screw with respect to the vertebra 3.

The entire length of the allograft strip 29 can be completely demineralized and an eyelet type device (not shown) formed of biocompatible material may be secured around the middle portion of the allograft strip 29 to serve as a barrier or grommet between the allograft strip 29 and the radial hole 8 of the pedicle screw shaft to lend structural strength to and protect the portion of the allograft strip 29 that contacts the radial holes 8 of the pedicle screw 7. Holes can alternatively be formed into the lamina at an appropriate angle and with appropriate care not to damage the adjacent neural elements or blood vessels, and the allograft strip 29 may be threaded through the radial holes 8 of the pedicle screw 7 and through or into the holes formed in the lamina. Suture threads or metal wire, e.g. titanium wire, etc., also can be used in place of the demineralized allograft strip 29.

Referring to FIG. 17, a pedicle screw 7 is disclosed that preferably includes a cannulated portion 9 extending from the proximal end of the pedicle screw 7 and terminating at one or more radial cut outs or slots 11 located at or near the midpoint along the pedicle screw's longitudinal axis. The slots 11 extend from the exterior of the pedicle screw to the interior cannulation. One or more partially or fully demineralized bone strips 56 may be fed from the proximal end 6, down the cannulation 9, and partially out the radial cut outs 11 using a simple instrument such as, for example, a plunger rod 50.

In the embodiment of FIG. 17, as the pedicle screw 7 advances into the vertebrae 3 and the slots 11 come into contact with the interior of the pedicle 4, the protruding allograft strips 56 are crushed against the interior of the pedicle 4. As the pedicle screw 7 is further advanced, the allograft bone strips 56 are pulled from the cannulated interior 9, out of the radial slots 11 and crushed against the interior of the pedicle 4 until the pedicle screw 7 is fully seated such that crushed allograft bone surrounds the threaded proximal exterior of the pedicle screw and additional purchase is provided. The one or more radial slots 11 may be disposed at or near the distal end of the pedicle screw 7 and the cannulated interior portion 9 may extend from the proximal end 6 and terminate at the radial slots 11. The radical slots may be provided at other locations along the shaft of the pedicle screw. Allograft bone strips 56 may be fed down the cannulation 9 and partially out the distal radial cut outs 11. As the pedicle screw 7 is advanced into bone, the allograft strips 56 are pulled out the distal radial slots 11 such that the crushed allograft bone surrounds the threaded shaft from the distal end to the proximal end. A flowable material may be injected into the threads of the screw 7 with a coupling mechanism that drives the screw 7 into the pedicle.

Figure 18:
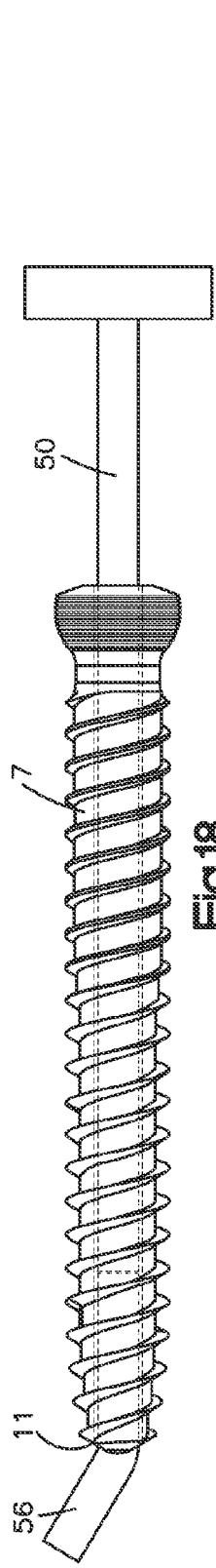
FIG. 18 illustrates a different, exemplary embodiment of a bone screw augmentation system in accordance with the present invention.

Referring to FIG. 18 a cannulated pedicle screw 7 preferably includes one or more radial slots 11 disposed at the end of the cannulation and/or somewhere between the distal end and the midpoint of the pedicle screw 7. In operation, the pedicle screw 7 is preferably fully inserted into a vertebral body 5 through the pedicle 4 and one or more partially demineralized allograft strips 56 are placed into the cannulated interior of the pedicle screw. A pusher rod 50 or other instrument is preferably placed at the proximal end 6 of the pedicle screw 7 and made to bear against the proximal end of the allograft strip 56 such that the distal end of the allograft bone strip 56 advances out of the radial cut out 11 preferably at an angle to the longitudinal axis of the screw 7, providing anchorage for the screw 7 into the cancellous interior of the vertebral body 3. The proximal end of the pedicle screw 7 is then preferably sealed with a plug formed of biocompatible material such as, for example, bone, stainless steel, or titanium, to prevent the one or more allograft strips 56 from backing out of the pedicle screw 7.

Figure 19A:
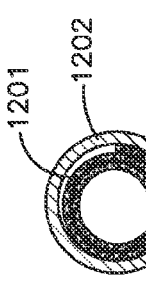
FIGS. 19A-D illustrate an exemplary embodiment of an insertion instrument in accordance with the present invention.
Figure 19B:
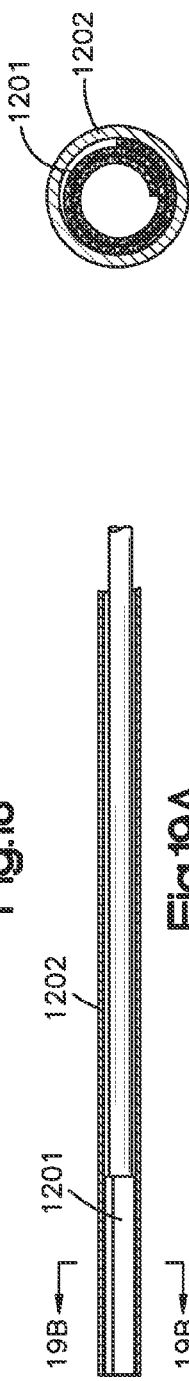
Figure 19C:
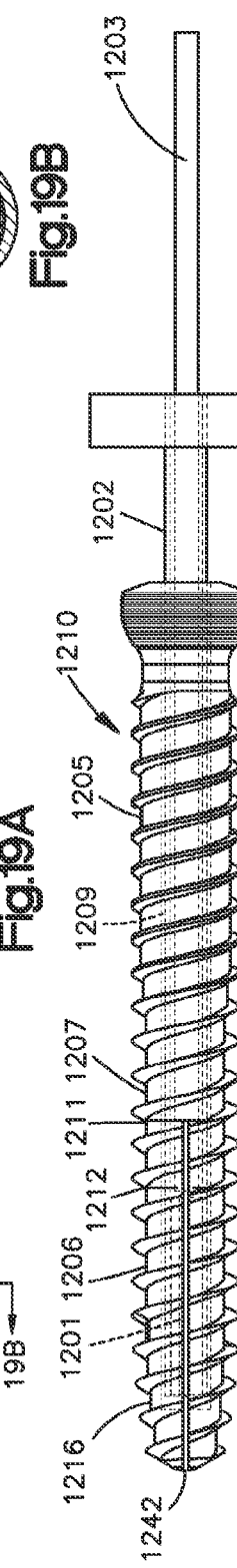

Referring to FIGS. 19A-D a pedicle screw 1207 in accordance with another embodiment includes a proximal portion 1205, a distal portion 1206 and a cannulated interior 1209 that extends through the proximal portion 1205 and at least partially into the distal portion 1206. A hinge mechanism 1211 preferably connects the distal portion 1206 and the proximal portion 1205 at or near the half way point along the longitudinal axis. The distal portion 1206 preferably includes slots 1242 along the longitudinal axis and into the cannulated interior 1209 such that a plurality, e.g., four, legs 1216, are formed and connected to one another using the flexible hinge mechanism 1211. Threading is preferably machined onto the external surfaces of the shaft of the screw 1207. In a first state, as shown in FIG. 19C, the four legs assume a closed position such that the distal portion 1206 is similar to a standard pedicle screw shaft. In operation, as shown in FIG. 19A, a compressed coil spring 1201 is preferably inserted under pressure into a long, hollow tube 1202. The coil spring 1201 is compressed and would expand if the tube 1202 did not hold the spring 1201 in its compressed state. The tube 1202 is preferably inserted into the cannulated interior 1209 of the pedicle screw 1207 such that the spring 1201 is located at or near the distal end 1206 of the pedicle screw 1207.

Figure 19D:
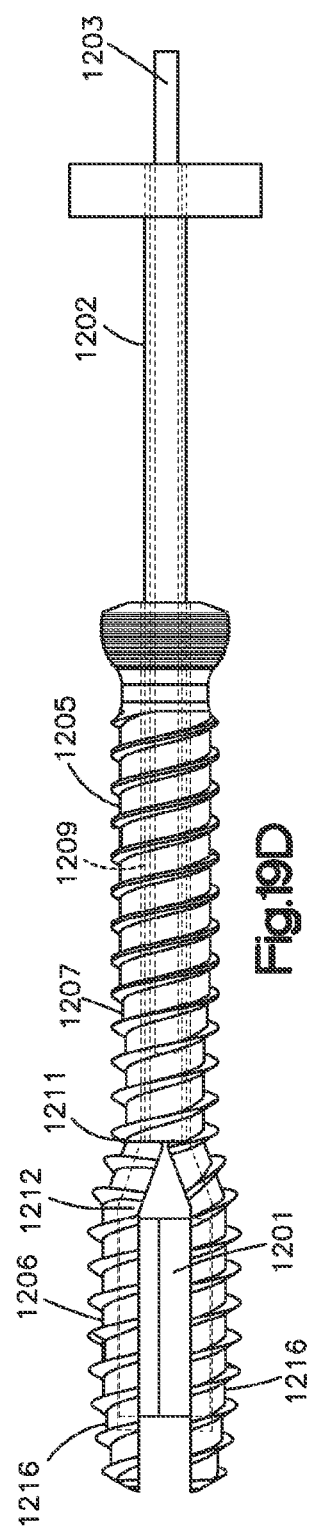

The pedicle screw 1207 is then preferably inserted into a vertebra 3 through a pedicle 4. A push rod 1203 as shown in FIG. 19C is preferably placed against the proximal end of the spring 1201 to hold the spring 1201 in position in the distal portion 1206 of the screw 1207 as the tube 1202 is withdrawn from the screw 1207. As the tube 1202 is retracted from the spring 1201, as shown in FIG. 19D, the spring 1201, which is held in the compressed state in the tube 1202, is no longer contained within the tube 1202 so the spring 1201 unwinds and pushes open the legs 1216 such that the distal portion 1206 is expanded preferably into the cancellous interior of the vertebra 3 and the pull-out strength of the pedicle screw 1207 is increased. The pedicle screw 1207 is illustrated with two hinge mechanisms 1211, 1212 as shown in FIG. 19D, although other hinge mechanisms and configurations are contemplated. In addition, while the bone augmentation screw 1207 has been shown as having four legs 1216, more or less legs 1216 may be utilized.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An implant configured to be positioned into bone tissue, the implant comprising:
a member, at least a portion of the member comprising allograft, the member adapted for insertion into the bone tissue, the member having a distal end, a proximal end spaced from the distal end along a central axis, an intermediate portion extending between the distal end and the proximal end, the implant defining a hollow cavity extending into the member at the proximal end, the hollow cavity extending along the central axis from the proximal end into the intermediate portion and toward the distal end, the member further defining an outer surface that extends from the proximal end to the distal end and is monolithic with each of the proximal end and the distal end, the member defining a plurality of recesses that each: 1) is disposed at least partially within the intermediate portion, 2) extends from the outer surface toward the hollow cavity, and 3) is spaced from adjacent ones of the plurality of recesses, the outer surface defining a cross-sectional dimension measured along a direction perpendicular to the central axis from the outer surface to the central axis;

wherein at least a portion of the member is at least partially demineralized, and at least a portion of the outer surface is expandable along the direction away from the central axis, such that the cross-sectional dimension of the member at the intermediate portion measured from a first location into the hollow cavity to the central axis is greater than the cross-sectional dimension at each of the proximal end and the distal end, the first location being located on the outer surface in the intermediate portion between adjacent ones of the plurality of recesses.

2. The implant of claim 1, comprising a proximal portion proximate the proximal end, and a distal portion proximate the distal end, wherein both the proximal and distal portions are configured to expand, and the distal portion is configured to expand more than the proximal portion.

3. The implant of claim 2, wherein the member is substantially cylindrically shaped having a substantially uniform outer diameter wherein the outer diameter is between about 2 mm and about 9 mm, the member length between about 10 mm and about 60 mm, with the distal portion between about 5 mm and about 50 mm in length, the proximal portion having a wall thickness between about 0.3 mm and about 1 mm, and the distal portion having a wall thickness between about 1 mm and about 2 mm.

4. The implant of claim 1, wherein the plurality of recesses include at least one of a slot, slit, cut, groove or perforation.

5. The implant of claim 4, wherein the plurality of recesses include at least three slots, wherein at least one of the slots is between about 10 mm and about 20 mm in length, and between about 1 mm and about 2 mm in width, wherein the width is measured perpendicular to the length.

6. The implant of claim 3, wherein the member is substantially cylindrically shaped, the distal portion defines a wall thickness, the proximal portion defines a wall thickness, and the wall thickness of the distal portion is greater than the wall thickness of the proximal portion.

7. The implant of claim 1 wherein the distal end is closed and defines a solid distal wall that has a depth, measured from the distal end toward the proximal end, of less than about 7 mm.

8. The implant of claim 7, wherein the closed distal end has a guide wire hole.

9. The implant of claim 7, wherein the solid distal wall of the closed distal end has a depth of about 3 mm.

10. The implant of claim 1 wherein the member is at least partially formed of freeze-dried allograft bone tissue.

11. The implant of claim 2, wherein the proximal portion is substantially cylindrically shaped and further comprises at least one of a slot, a slit, a cut, a groove, or a perforation.

12. The implant of claim 2, further comprising at least one of a slot, slit, groove or perforation that is configured to form a parting line in the distal portion that is configured to tear and form expandable fingers upon insertion of at least one of a bone screw, a bone pin, or a bone dowel into the hollow cavity.

13. The implant of claim 1, further comprising a continuous ring wall formed at the proximal end, and a plurality of strips extending from the continuous ring wall.

14. The implant of claim 2, wherein the distal portion has a plurality of strips connected by a continuous ring wall at the distal end, the plurality of strips having a thinned section that acts as a hinge and a preferential fold line, whereby the continuous ring wall is moveable to form an expanded distal portion having folded strips.

15. The implant of claim 2, wherein the distal portion has a continuous wall forming a distal ring section, and the member further includes a mid-section having at least one of slots, slits, grooves or perforations to facilitate expansion of the mid-section, the mid-section having a larger wall thickness than both the proximal portion and distal ring section.

16. The implant of claim 1, wherein at least a portion of the implant is formed from at least one of a thermoplastic elastomer, rubber, titanium, stainless steel, titanium alloy, metal alloys, or ceramic.

17. The implant of claim 16, wherein the thermoplastic elastomer is at least one of PEEK, PCU, PCL, and EVA.

18. The implant of claim 2, wherein the direction is a first direction, the implant, further including a protrusion extending from the proximal end of the member in a second direction away from the distal portion, the protrusion configured to restrict rotation or translation of the member relative to a fastener as the fastener is inserted into the hollow cavity.

19. The implant of claim 1, wherein as the outer surface expands a distance between the proximal end and the distal end decreases.

20. The implant of claim 1, wherein an entirety of the member is made from allograft.

21. The implant of claim 1, wherein the hollow cavity extends through the distal end.

22. The implant of claim 1, wherein the member further defines a second location on the outer surface that is disposed in the intermediate portion, the outer surface defines an outer dimension measured along the direction perpendicular to the central axis, and at least a portion of the outer surface is expandable along the direction away from the central axis, such that the outer dimension of the member at the intermediate portion measured from the first location through the hollow cavity and the central axis to the second location is greater than the outer dimension at each of the proximal end and the distal end.

23. The implant of claim 1, wherein the at least a portion of the outer surface is expandable along the direction away from the central axis such that the cross-sectional dimension of the outer surface at the intermediate portion before expansion is less than the cross-sectional dimension of the outer surface at the intermediate portion after expansion.

24. A bone implant comprising:
a member, at least a portion of the member comprising allograft, the member configured to be inserted into bone tissue, the member having a distal end, a proximal end spaced from the distal end along a central axis that extends from the proximal end to the distal end such that the member is elongate along the central axis, the proximal end including a proximal opening, and the member defining a hollow cavity that extends from the proximal opening toward the distal end along the central axis, the proximal end including an inner surface facing the central axis, an outer surface opposite the inner surface, and a thickness measured from the inner surface to the outer surface in a first direction that is perpendicular to the central axis, the hollow cavity sized to receive a fastener that imparts a force onto the member as it is received in the hollow cavity; and
a protrusion that extends from the proximal end in a second direction that is substantially parallel to the central axis, such that the proximal end is disposed between the distal end and at least a portion of the protrusion with respect to the second direction, the protrusion includes a protrusion inner surface facing the central axis, a protrusion outer surface opposite the protrusion inner surface, and a thickness measured from the protrusion inner surface to the protrusion outer surface in the first direction, the protrusion configured to be held by an insertion instrument such that the protrusion receives a counterforce to the force imparted onto the member by the fastener as the hollow cavity receives the fastener;

wherein the thickness of the protrusion is substantially equal to the thickness of the proximal end, and the bone implant is devoid of a second protrusion that extends from the proximal end at a position opposite the protrusion with respect to the first direction.

25. The implant of claim 18, wherein the protrusion includes a tab having an inner surface facing the central axis and an outer surface opposite the inner surface.

26. The bone implant of claim 24, wherein the protrusion includes a tab, and the fastener includes one of a bone screw or a bone pin.

27. The bone implant of claim 24, wherein the protrusion is flexible, such that the protrusion is movable in a direction away from the central axis.

28. The bone implant of claim 27, the protrusion is flexible such that the protrusion is movable in a direction away from the central axis such that at least a portion of the protrusion is positioned farther from the central axis than the outer surface of the proximal end.

29. The bone implant of claim 24, wherein the protrusion extends away from the proximal end of the member such that when the implant is positioned within the hollow cavity and the fastener is inserted into the hollow cavity, the protrusion remains at least partially outside the hollow cavity.

30. The bone implant of claim 24, wherein the protrusion is monolithic with the member.

31. The bone implant of claim 24, wherein at least a portion of the protrusion is made of at least one of allograft bone tissue, a thermoplastic elastomer, rubber, titanium, stainless steel, titanium alloy, metal alloys, or ceramic.

32. The bone implant of claim 24, wherein at least a portion of the member is at least partially demineralized.

33. The bone implant of claim 24, wherein the protrusion presents a grip surface that extends from the proximal end such that the proximal end is disposed between the distal end and at least a portion of the grip surface.

34. A bone implant comprising:
a member, at least a portion of the member comprising allograft, the member configured to be inserted into bone tissue, the member having a distal portion and a proximal portion that is spaced from the distal portion along a central axis that extends from the proximal portion to the distal portion such that the member is elongate along the central axis, the bone implant defining a proximal opening that extends into the proximal portion and a hollow cavity that extends from the proximal opening toward the distal portion along the central axis;
wherein the member is expandable, and at least a portion of the member is at least partially demineralized such that the proximal portion is demineralized to a greater extent than the distal portion.

35. The implant of claim 34, wherein at least a portion of the distal portion is nondemineralized.

36. The implant of claim 34, wherein at least a portion of the proximal portion is at least 80% demineralized.

37. The implant of claim 36, wherein an entirety of the proximal portion is at least 80% demineralized.

38. The implant of claim 34, wherein the member is expandable in a direction perpendicular to the central axis.

39. The implant of claim 34, wherein the hollow cavity is configured to receive a fastener, and the member is configured to expand in a radial direction perpendicular to the central axis as the hollow cavity receives the fastener.

40. The implant of claim 34, wherein the proximal portion is expandable in the radial direction to a greater extent without breaking than the distal portion.

41. The implant of claim 34, wherein the distal portion is closed such that the distal portion defines a solid distal wall that has a depth, measured from a distal end of the implant toward a proximal end of the implant.

42. The implant of claim 34, further including a protrusion extending from the proximal portion of the member in a direction away from the distal portion.

43. A bone implant comprising:
a member, at least a portion of the member comprising allograft, the member configured to be inserted into bone tissue, the member having a distal portion including a distal end, a proximal portion including a proximal end, the distal portion spaced from the proximal portion along a central axis that extends from the proximal end to the distal end such that the member is elongate along the central axis, the proximal end including a proximal opening, the bone implant defining a hollow cavity that extends from the proximal opening along the central axis toward the distal end, the member having an inner surface that at least partially defines the hollow cavity and an outer surface opposite the inner surface,
wherein 1) the member defines a wall thickness measured between the inner surface and the outer surface in a first direction that is perpendicular to the central axis, such that the wall thickness at the distal portion is greater than the wall thickness at the proximal portion, 2) the outer surface of the member extends from the proximal end to the distal end along at least one straight line that extends from the proximal end to the distal end in a second direction that is parallel to the central axis, and the outer surface is substantially smooth such that the outer surface is devoid of any indentations, ridges, or gaps that intersect with the at least one straight line, and 3) at least a portion of the member is at least partially demineralized.

44. The implant of claim 43, wherein the outer surface defines an outer dimension measured along the first direction, and the member is expandable such that the outer dimension of the member in the distal portion is greater than the outer dimension at the proximal portion.

45. The implant of claim 43, wherein the distal end is closed and defines a solid distal wall that has a depth, measured from the distal end toward the proximal end.

46. The implant of claim 43, further including a protrusion extending from the proximal end of the member in a direction away from the distal portion, the protrusion configured to restrict rotation or translation of the member relative to a fastener as the fastener is inserted into the hollow cavity.

47. The implant of claim 46, wherein the protrusion includes a tab having an inner surface facing the central axis and an outer surface opposite the inner surface.

48. An implant configured to be positioned into bone tissue, the implant comprising:
a member, at least a portion of the member comprising allograft, the member adapted for insertion into the bone tissue, the member having a distal end, a proximal end spaced from the distal end along a central axis, an intermediate portion extending between the distal end and the proximal end, the implant defining a hollow cavity extending into the member at the proximal end, the hollow cavity extending along the central axis from the proximal end into the intermediate portion and toward the distal end, the member further defining an outer surface that extends from the proximal end to the distal end and is monolithic with each of the proximal end and the distal end, the outer surface defining an outer dimension measured along a direction perpendicular to the central axis, the member defining at least one recess that extends from the outer surface toward the hollow cavity, such that the at least one recess interrupts the outer surface;

wherein at least a portion of the member is at least partially demineralized, and at least a portion of the outer surface is expandable away from the central axis along an entirety of a circumferential line that 1) lies on the outer surface, 2) is spaced from the recess along the central axis, and 3) lies in a plane normal to the central axis, such that the outer dimension of the member at the intermediate portion is greater than the outer dimension at each of the proximal end and the distal end.

49. The implant of claim 48, wherein the at least one recess includes a plurality of recesses that each: 1) are disposed at least partially within the intermediate portion, and 2) are spaced from adjacent ones of the plurality of recesses, the member further defining a first location on the outer surface that is disposed in the intermediate portion between adjacent ones of the plurality of recesses, and a second location on the outer surface that is disposed in the intermediate portion, and the outer dimension of the intermediate portion is measured from the first location through the hollow cavity and the central axis to the second location.

50. The implant of claim 49, wherein the member is expandable such that the outer dimension of the member at the intermediate portion measured from the first location through the hollow cavity and the central axis to the second location is greater than the outer dimension at each of the proximal end and the distal end.

51. The implant of claim 48, wherein the direction is a first direction, the implant, further comprising a protrusion that extends from the proximal end in a second direction that is substantially parallel to the central axis, such that the proximal end is disposed between the distal end and at least a portion of the protrusion with respect to the direction that is substantially parallel to the central axis.

52. The implant of claim 48, wherein the at least one recess that extends from the outer surface into the hollow cavity.

53. The implant of claim 48, wherein the outer surface defines a cross-sectional dimension measured along the direction from the outer surface to the central axis, and at least a portion of the outer surface is expandable along the direction away from the central axis, such that the cross-sectional dimension of the member measured from a first location into the hollow cavity to the central axis is greater than the cross-sectional dimension at each of the proximal end and the distal end, the first location being located on the outer surface in the intermediate portion even with the at least one recess along the central axis.

* * * * *